(12) United States Patent
Pinet et al.

(10) Patent No.: US 7,897,406 B2
(45) Date of Patent: Mar. 1, 2011

(54) METHOD AND SENSOR FOR DETECTING A CHEMICAL SUBSTANCE USING AN OPTICALLY ANISOTROPIC MATERIAL

(75) Inventors: Éric Pinet, Val-Bélair (CA); Gaétan Duplain, Beauport (CA)

(73) Assignee: FISO Technologies Inc., Quebec (CA)

( * ) Notice: Subject to any disclaimer, the term of this patent is extended or adjusted under 35 U.S.C. 154(b) by 1361 days.

(21) Appl. No.: 10/539,771

(22) PCT Filed: Dec. 19, 2003

(86) PCT No.: PCT/CA03/01996

§ 371 (c)(1),
(2), (4) Date: Jan. 10, 2006

(87) PCT Pub. No.: WO2004/057314

PCT Pub. Date: Jul. 8, 2004

(65) Prior Publication Data

US 2006/0141466 A1 Jun. 29, 2006

(30) Foreign Application Priority Data

Dec. 20, 2002 (CA) .................................. 60434780

(51) Int. Cl.
*G01N 33/00* (2006.01)
(52) U.S. Cl. ............................ 436/164; 422/50; 422/55; 422/57; 422/58; 422/68.1; 422/82.02; 422/99
(58) Field of Classification Search .................. 422/50, 422/55, 57, 58, 68.1, 82.02, 99; 436/164
See application file for complete search history.

(56) References Cited

U.S. PATENT DOCUMENTS

| 2,106,744 A | 2/1938 | Hood et al. |
| 2,221,709 A | 11/1940 | Hood et al. |
| 2,286,275 A | 6/1942 | Hood et al. |
| 4,146,887 A | 3/1979 | Hagnante |
| 4,154,586 A | 5/1979 | Jones et al. |
| 4,155,358 A | 5/1979 | McAllister et al. |
| 4,326,514 A | 4/1982 | Eian |
| 4,530,706 A | 7/1985 | Jones |
| 4,597,942 A | 7/1986 | Meathrel |

(Continued)

FOREIGN PATENT DOCUMENTS

EP 0536656 5/2000

(Continued)

OTHER PUBLICATIONS

Gelb, L.D. et al, "Phase Separation in Confined Systems", Rep. Prog. Phys. 62, 1999, pp. 1573-1660.

(Continued)

*Primary Examiner*—Sam P Siefke
(74) *Attorney, Agent, or Firm*—McDermott Will & Emery LLP

(57) ABSTRACT

A method and sensor for detecting a chemical substance in an analyte. An anisotropic material is subjected to the analyte. Light is passed through the anisotropic material and collected. A change of an optical anisotropy of the collected light is detected, the change being indicative of the chemical substance in the analyte.

91 Claims, 18 Drawing Sheets

U.S. PATENT DOCUMENTS

| | | | |
|---|---|---|---|
| 4,631,952 | A | 12/1986 | Donaghey |
| 4,684,380 | A | 8/1987 | Leichnitz |
| 4,699,511 | A | 10/1987 | Seaver |
| 4,732,480 | A | 3/1988 | Fortunato et al. |
| 4,834,496 | A | 5/1989 | Blyler, Jr. et al. |
| 4,846,548 | A | 7/1989 | Klainer |
| 4,847,594 | A | 7/1989 | Stetter |
| 4,940,328 | A | 7/1990 | Hartman |
| 4,998,017 | A | 3/1991 | Ryan et al. |
| 5,015,843 | A | 5/1991 | Seitz et al. |
| 5,206,118 | A | 4/1993 | Sidney et al. |
| 5,238,729 | A | 8/1993 | Debe |
| 5,250,095 | A | 10/1993 | Sigel, Jr. et al. |
| 5,268,305 | A * | 12/1993 | Ribi et al. ............ 436/501 |
| 5,308,771 | A | 5/1994 | Zhou et al. |
| 5,338,415 | A | 8/1994 | Sailor et al. |
| 5,436,167 | A | 7/1995 | Robillard |
| 5,453,624 | A | 9/1995 | Sailor et al. |
| 5,512,882 | A | 4/1996 | Stetter et al. |
| 5,525,800 | A | 6/1996 | Sanghera et al. |
| RE35,355 | E | 10/1996 | Ryan et al. |
| 5,659,296 | A | 8/1997 | Debe et al. |
| 5,783,836 | A | 7/1998 | Liu et al. |
| 5,828,798 | A | 10/1998 | Hopenfeld |
| 6,007,904 | A | 12/1999 | Schwotzer et al. |
| 6,031,454 | A | 2/2000 | Lovejoy et al. |
| 6,130,748 | A | 10/2000 | Kruger et al. |
| 6,248,539 | B1 | 6/2001 | Ghadiri et al. |
| 6,278,106 | B1 | 8/2001 | Muto et al. |
| 6,375,725 | B1 | 4/2002 | Bernard et al. |
| 6,432,721 | B1 | 8/2002 | Zook et al. |
| 6,610,977 | B2 | 8/2003 | Megerle |
| 6,707,561 | B1 * | 3/2004 | Budach et al. ............ 356/521 |
| 6,951,715 | B2 * | 10/2005 | Cunningham et al. ........ 435/4 |
| 2003/0180966 | A1 * | 9/2003 | Abbott et al. ............ 436/518 |

FOREIGN PATENT DOCUMENTS

| | | |
|---|---|---|
| WO | WO 0222237 | 3/2002 |

OTHER PUBLICATIONS

Gross, E. et al "Highly Sensitive Recognition Element Based on Birefringent Porous Silicon Layers", J. Appl. Phys. 90 No. 7, 2001, pp. 3529-3532.

Gao, J. et al., "Vapor Sensors Based on Optical Interferometry From Oxidized Microporous Silicon Films" Langmuir 18, 2002, pp. 2229-2233.

Gao, J. et al, "Porous-Silicon Vapour Sensor Based on Laser Interferometry" Appl. Phys. Lett. vol. 77 n6, 2000, pp. 901-903.

Canham, L.T, "Properties of Porous Silicon", Canham L. Ed., EMIS Data reviews series No. 18, 1997, INSPEC publ, pp. 154-157.

Bjorklund, R.B., et al., "Color changes in thin porous silicon films caused by vapor exposure", Appl. Phys. Let. 69(20), 1996, pp. 3001-3003.

Zangooie, S. et al., "Vapor sensitivity of thin porous silicon layers", Sensors and Actuators B 43, 1997, pp. 168-174.

Zangooie, S., et al., "Reversible and irreversible control of optical properties of porous silicon superlattices by thermal oxidation, vapour adsorption, and liquid penetration", J. Vac. Sci, Technol. A 16(5), 1998, pp. 2901-2912).

Takamori, T., "Structural anisotropy and birefringence in microporous glasses", j. Am. Ceram. Soc. 61 No. 9-10, 1978, pp. 434-438.

Ryoo, R. et al., "Optically transparent, single-crystal-like oriented mesoporous silica films and plates", J. Phys. Chem. B 101, 1997, pp. 10610-10613.

Ko, C.H., et al., "Mesocrystal engineering using non-bonded interaction to obtain optically transparent mesoporous silica films and plates with uniform orientation", Micro. Meso. Mat. 21, 1998, pp. 235-243.

Takamori, T. et al. "Anomalous birefringence in oxide glasses" in "treatise on materials science and technology", Glass 1 vol. 12, 1997, pp. 123-155, Tomozawa M. & Doremus R.H. Eds., Academic Press N.Y.

Antropova, T.V., et al. "Porous glass: inhomogeneities and light transmission", Opt. Appl. vol. XXX No. 4, 2000, 553-567.

Altshuler, G.B., et al., "Spatial dispersion of anisotropy of high-silica microporous glasses", Opt. Spektrosk. 63, 1987, 228-231.

Altshuler, G.B., et al., "Porous glass optics", J. Non-Cryst. Solids 123, 1990, pp. 266-270.

Burkat, T.M., et al., "Structural anisotropy and birefringence in porous glass plates", Fiz. Khim. Stekla 17 No. 5, 1991, pp. 781-790.

Herman, P.H. In Colloid Science, 1949, vol. II, Reversible Systems, H.R. Kruyt Ed., Elsevier Pub. Chap. XII § 6 "Sorption and swelling", pp. 512-580.

Foltynowicz, Z, et al. "Effect of silane treatment on the pore structure of porous glasses", Glass Technology Vo. 34, No. 5, 1993, pp. 206-209.

Lorkowski, H.J., et al., "Optical Polymers with special birefringent properties", Polymers for Advanced Technologies vol. 7, 1996, pp. 501-506.

Li, Y.Y., et al., "Polymer replicas of photonic porous silicon for sensing and drug delivery applications", Science Vo. 299, 2003, pp. 2045-2047.

Beom-Hoan O et al., "Vapor Sensor Realized in an Ultracompact Polarization Interferometer Built of a Freestanding Porous-Silicon Form Birefringent Film", IEEE Photonics Technology Letters, IEEE Inc., New York, US, vol. 15, No. 6, Jun. 2003 pp. 834-836, XP001175197.

Liu R et al., "Novel Porous silicon vapor senseor based on polarization interferometry" Sensors and Actuators B, Elsevier Sequoia S.A., Lausanne, CH, vol. 87, No. 1, Nov. 15, 2002, pp. 58-62 XP 004391077.

Rong Liu et al., "Porous silicon vapor sensor based on polarization interferometry" LEOS 2001. 14th Annual Meeting of the IEEE Lasers & Electro-Optics Society. San Diego, CA, Nov. 11-15, 2001, Annual Meeting of the IEEE Lasers and Electro-Optics Society, New York, NY: IEEE, US, vol. 1-2, pp. 820-821, XP010566702.

Kooyman R P H et al., "Optical fiber immunosensor based on polarimetry" Transducers. San Francisco, Jun. 24-27, 1991, Proceedings of the International Conference on Solid State Sensors Andactuators, New York, IEEE, US, vol. Conf. 6, Jun. 24, 1991, pp. 376-377, XP010037367.

Heideman R G et al., "Polarimetric Optical-Fibre Sensor for Biochemical Measurements" Sensors and Actuators B, Elsevier Sequoia S.A., Lausanne, CH, vol. B12, No. 3, Apr. 15, 1993, pp. 205-212, XP 000397509.

Veldhuis G J et al., "An integrated optical Bragg-reflector used as a chemo-optical sensor" Pure and Applied Optics, Bristol, GB, vol. 7, No. 1, 1998, pp. L23-L26, XP 002087839.

\* cited by examiner

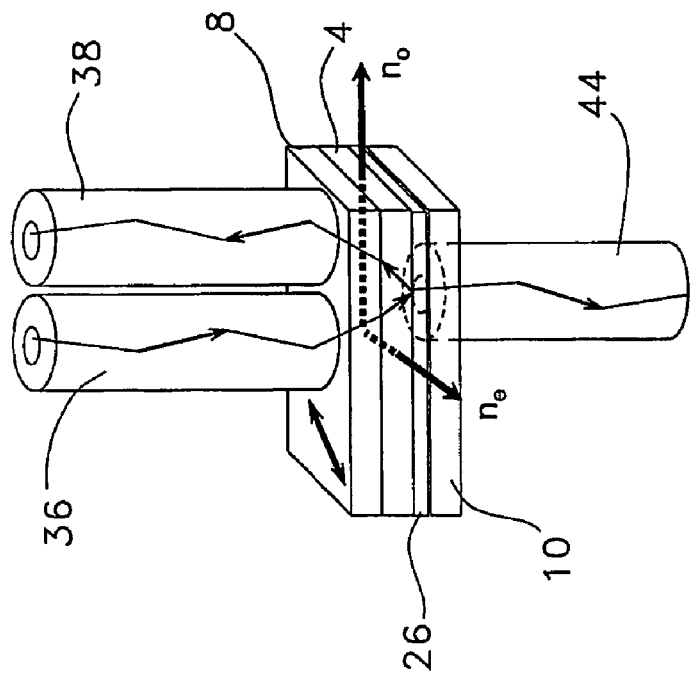
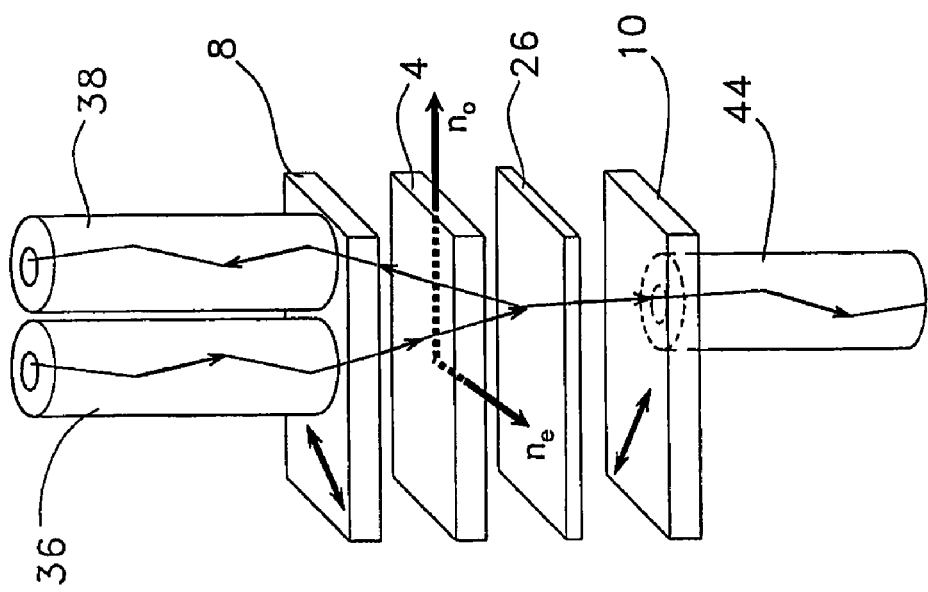
FIG. 14A
FIG. 14B

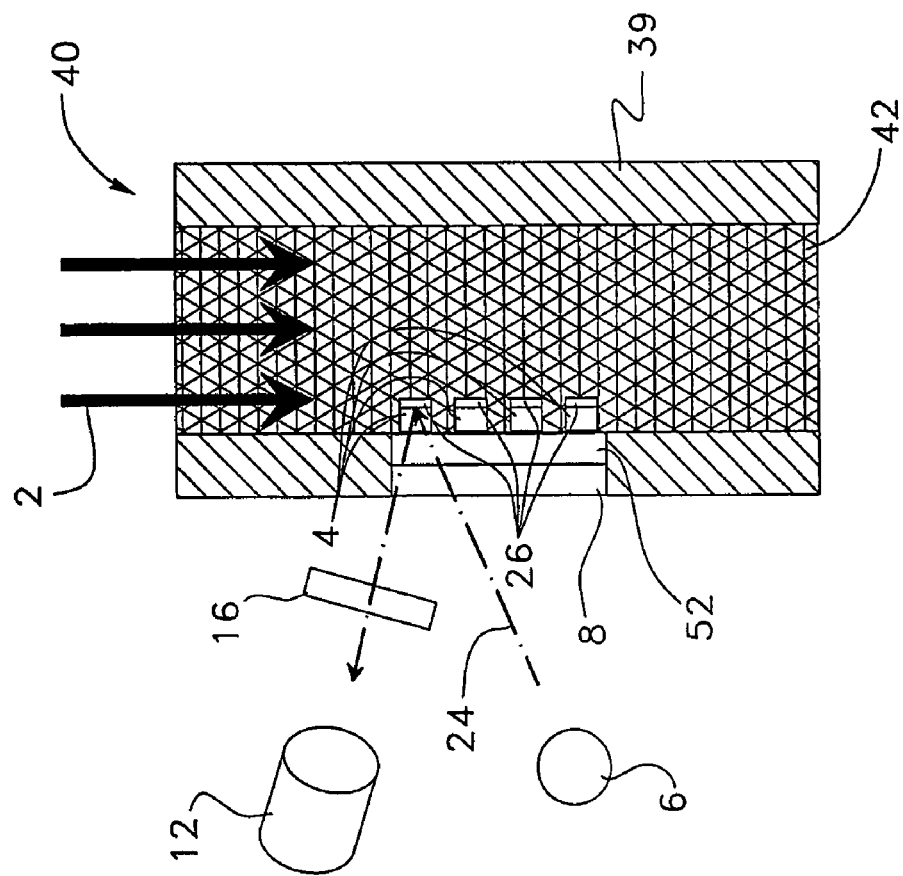
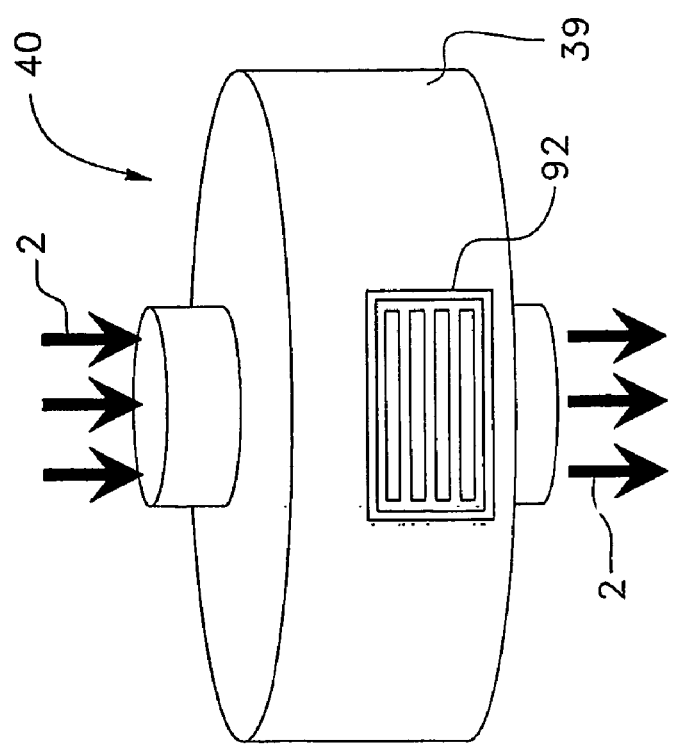

METHOD AND SENSOR FOR DETECTING A CHEMICAL SUBSTANCE USING AN OPTICALLY ANISOTROPIC MATERIAL

FIELD OF THE INVENTION

The present invention relates to a method and a sensor for detecting a chemical substance, and to a method and a sensor for detecting a presence of liquid, gas or vapor of a chemical substance through changes in an optically anisotropic material upon exposure to such liquid, gas or vapor. The method and the sensor have applications such as an end-of-service-life indicator which may be incorporated in an air purifying device so as to provide a warning when the life of a filter is near to exhaustion. It may also be used as a remaining-life indicator, a dosimeter, etc.

BACKGROUND

Chemical detection is often mandatory for industrial or safety applications and simple, reliable sensors should be implemented for process control or for security monitoring.

A number of chemical sensors for detection of chemicals are already known in the art, based on changes in characteristics such as physical, chemical, electrochemical or optical properties.

Chemical detection may be performed using electronic methods. For example, composite polymers having their electrical impedance changing upon exposure to vapors (e.g. commercial products made by the company Cyrano Sciences Inc.) may be used for this purpose. U.S. Pat. No. 5,512,882 (Stetter et al.), U.S. Pat. No. 4,631,952 (Donaghey), and U.S. Pat. No. 5,238,729 (Debe) show examples of chemical sensors of this type. In general, these types of sensing methods require a large variety of polymers or other types of materials with a selection of responses depending on the chemical species to detect, making them more complicated to produce and to use.

U.S. Patent No. 4,846,548 (Klainer), U.S. Pat. No. 5,828,798 (Hopenfeld), U.S. Pat. No. 6,278,106 (Muto et al.), U.S. Pat. No. 4,834,496 (Blyler, Jr. et al.), U.S. Pat. No. 5,436,167 (Robillard), U.S. Pat. No. 4,699,511 (Seaver), U.S. Pat. No. 4,940,328 (Hartman), U.S. Pat. No. 6,007,904 (Schwotzer et al.), U.S. Pat. No. 5,783,836 (Liu et al.), U.S. Pat. No. 5,015,843 (Seitz et al.), U.S. Pat. No. 5,308,771 (Zhou et al.), U.S. Pat. No. 4,998,017 and Re. 35,355 (Ryan et al.), U.S. Pat. No. 5,525,800 (Sanghera et al.), U.S. Pat. No. 4,732,480 (Fortunato et al.) and European patent EP 0 536 656 (Guenter et al.) show examples of optically based chemicals sensors and apparatus including fiber optic chemical sensors (FOCS).

A number of these FOCS use changes in the guiding properties of the optical fiber, including transmission parameters such as intensity, ellipticity and reflective or refractive angles. Many of the optical methods involved in the above sensors and apparatus require specific cladding or coating materials depending on the chemical species to be detected, which make them not very practical in industrial applications where different chemical species may be present. Some difficulties may arise during development of such chemically reacting cladding or coating such as compatibility of the reactive molecules with the desired refractive index range value, or adhesion problems between the core and the reactive cladding or coating of such fibers. Their applications may thus be limited to specific configurations.

Many of the optical chemical sensors use a spectroscopic approach and rely on light absorption at specific wavelengths to detect chemical species. Such spectroscopic approaches can be a very powerful tool for chemical characterization and quantification but are usually expensive and difficult to implement, and require usually some good knowledge for adjustments and for data interpretation.

In order to increase the contact surface of the sensor with chemicals to be detected, porous materials with high surface area are often used. Capillary condensation and use of porous silicon as sensing material are described in the literature (see e.g. Gelb, L. D. et al., "Phase separation in confined systems", Rep. Prog. Phys. 62, 1999, pp. 1573-1660; Gross, E. et al., "Highly sensitive recognition element based on birefringent porous silicon layers", J. Appl. Phys. 90 No. 7, 2001, pp. 3529-3532; Liu, R. et al., "Novel porous silicon vapour sensor based on polarization interferometry" Sensors and Actuators B 87, 2002, pp. 58-62; Gao, J. et al., "Vapor sensors based on optical interferometry from oxidized microporous silicon films" Langmuir 18, 2002, pp. 2229-2233; Gao, J. et al., "Porous-silicon vapour sensor based on laser interferometry" Appl. Phys. Lett. Vol. 77 n°6, 2000, pp. 901-903; Canham, L. T., "Properties of Porous Silicon", Canham L. Ed., EMIS Data reviews series No. 18, 1997, INSPEC publ., pp. 154-157; Bjorklund, R. B. et al., "Color changes in thin porous silicon films caused by vapor exposure", Appl. Phys. Lett. 69 (20), 1996, pp. 3001-3003; Zangooie, S. et al., "Vapor sensitivity of thin porous silicon layers", Sensors and Actuators B 43, 1997, pp. 168-174; Zangooie, S. et al. "Reversible and irreversible control of optical properties of porous silicon superlattices by thermal oxidation, vapour adsorption, and liquid penetration" J. Vac. Sci. Technol. A 16(5), 1998, pp. 2901-2912); as well as in the U.S. Pat. No. 6,130,748 (Kruger et al.), U.S. Pat. No. 6,248,539 (Ghadiri et al.), U.S. Pat. No. 5,338,415 (Sailor et al.) and U.S. Pat. No. 5,453,624 (Sailor et al.). Porous glass can also be used as described in U.S. Pat. No. 5,250,095 (Sigel, Jr. et al.) and U.S. Pat. No. 6,375,725 (Bernard et al.).

In cases where porous materials such as porous silicon films are used, fragility due to high porosity (e.g. usually over 50-80%) associated with small film thicknesses (e.g. typically 10-100 μm) makes them brittle and less attractive for industrial applications where robust sensors are required, especially if they must be embedded inside an absorbent material. Besides aging problems related to surface oxidation and chemical stability, another drawback of porous silicon sensors is that spectral shifts occur in the far red and near infrared region (~800-1700 nm) which means that the human eye could not be used as a light detector. However in some cases, color changes, characterized by ellipsometry, are related to the refractive index of the solvents condensing into the pores and replacing air. Since lower partial pressures of solvent cause no color changes in the film, only the variation in the ellipsometric angles at certain energies could be applied to sensing applications.

Air purifying devices, including air purifying respirator cartridges and canisters, are widely used in the civil and military industries to protect the workers against harmful effects of toxic materials. Such devices usually consist of a filter chamber filled with adsorbent material that traps (e.g. adsorbs or absorbs) vapors or gases on its surface or within its porous structure. As the adsorbent material is completely filled, the air-purifying device loses protective capability for the user against the contaminant. This could have dramatic effects, especially when the contaminant has poor warning properties, e.g. if its odor, taste or irritation limit is greater than the permissible exposure limit or if there is insufficient toxicological data to determine an exposure limit.

In establishing new certification standards in 1984, the U.S. National Institute for Occupational Safety and Health (NIOSH) encouraged the development of active end-of-service-life indicators. Such indicators should detect the presence of contaminants and provide an unambiguous signal warning the user that the filter of the air-purifying device is almost exhausted. Examples of chemical sensors proposed for use as end-of-service-life indicators are shown in U.S. Pat. No. 4,154,586 (Jones et al.) and U.S. Pat. No. 4,530,706 (Jones), U.S. Pat. No. 4,684,380 (Leichnitz), U.S. Pat. No. 4,326,514 (Eian), U.S. Pat. No. 5,659,296 (Debe et al.), U.S. Pat. No. 4,155,358 (McAllister et al.), U.S. Pat. No. 4,146,887 (Magnante), U.S. Pat. No. 4,847,594 (Stetter), U.S. Pat. No. 6,375,725 (Bernard et al.) and in international application No. WO 02/22237 (Curado et al.).

End-of-service-life indicators may involve a visual color change that warns the user to replace the filter. Such color changes are sometimes induced by chemical reactions of a usually single use color indicator. One drawback of such chemical color indicators is that they are usually very specific to the chemical or class of chemicals (such as acids) they should react with.

SUMMARY

According to one aspect of the present invention, there is provided a method for detecting a chemical substance in an analyte, comprising steps of: subjecting an optically anisotropic material at least partially surrounded by absorbent particles to the analyte; passing light through the anisotropic material; collecting at least a portion of the passed light; and detecting a change in an optical anisotropy of the collected light, the change being indicative of the chemical substance in the analyte.

According to another aspect of the present invention, there is also provided a sensor for detecting a chemical substance in an analyte, comprising: an optically anisotropic material at least partially surrounded by absorbent particles to be subjected to the analyte; a light supply passing light through the anisotropic material; a collector capturing at least a portion of the passed light; and a detector characterizing or quantifying a change in an optical anisotropy of the collected light, the change being indicative of the chemical substance in the analyte.

According to another aspect of the present invention, there is also provided a method for detecting a chemical substance in an analyte, comprising steps of: subjecting an optically anisotropic material to the analyte; passing visible light through the anisotropic material; collecting at least a portion of the passed visible light; and detecting a change in a polarization state of the collected visible light, the change being indicative of the chemical substance in the analyte.

According to another aspect of the present invention, there is also provided a sensor for detecting a chemical substance in an analyte, comprising: an optically anisotropic material to be subjected to the analyte; a light supply passing visible light through the anisotropic material; a collector capturing at least a portion of the passed visible light; and a detector characterizing or quantifying a change in a polarization state of the collected visible light, the change being indicative of the chemical substance in the analyte.

According to another aspect of the present invention, there is also provided a method for detecting a chemical substance in an analyte, comprising steps of: subjecting an optically anisotropic material other than porous silicon to the analyte; passing light through the anisotropic material; collecting at least a portion of the passed light; and detecting a change in an optical anisotropy of the collected light, the change being indicative of the chemical substance in the analyte.

According to another aspect of the present invention, there is also provided a sensor for detecting a chemical substance in an analyte, comprising: an optically anisotropic material other than porous silicon to be subjected to the analyte; a light supply passing light through the anisotropic material; a collector capturing at least a portion of the passed light; and a detector characterizing or quantifying a change in an optical anisotropy of the collected light, the change being indicative of the chemical substance in the analyte.

The following provides a non-restrictive summary of certain features of the invention which will be more fully described hereinafter.

The invention utilizes changes of optical anisotropy that occur in certain classes of materials, especially but not restrictively porous optical materials such as porous glass and polymeric materials, upon exposure to liquid, gases or vapors of chemical substances. The change of optical anisotropy can be observed for example as optical birefringence, dichroism or selective absorption, anisotropic diffusion of light or anisotropic scattering of light.

As one example of an anisotropic material, a porous glass exhibiting optical birefringence may be used to detect liquids, gases or vapors. The porous glass may be made from a phase separation process followed by chemical etching through which the optical birefringence may be controlled. Adsorption of liquid by imbibition into the pores or of gas or vapor molecules by capillary condensation into the pores changes for example the optical birefringence of the porous glass, causing a porosity-induced change in optical anisotropy that may be detected using several methods. The change may for example be detected by observing a color shift of the light transmitted through the porous glass placed between two crossed polarizers, or by comparing the transmitted light intensity at different wavelengths.

An optically birefringent multilayer porous thin film may also be used as the anisotropic material. The optical birefringence of the multilayer thin film changes in the same manner as with porous glass and may be detected in the same manner.

An optically birefringent polymer, an optically birefringent polymer composite, or an optically birefringent multilayer polymer film may also be used. The optical birefringence of the polymer may for example change in the presence of a chemical substance due to swelling of the polymer. These changes may be measured in the same manner as with porous glass.

An optically dichroic polymer, or an optically dichroic polymer composite, or an optically dichroic multilayer polymer film may also be used. The dichroism of the polymer may for example change in the presence of a chemical substance due to swelling of the polymer. These changes may be observed by measuring the intensity changes of a given polarization state of light or by measuring changes in the ratio of intensities of two mutually orthogonal states of polarization.

An optical anisotropically scattering or an optical anisotropically diffusing material, such as porous glass or a composite polymer, may be used. The optical anisotropy of the scattering of light or of the diffusion of light may be affected in the same manner as mentioned above in the case of porous material (glass, thin film, etc.) or in the case of a polymer. Polarization-dependent scattering or diffusion changes may for example be observed by measuring changes in the intensity of a given polarization state of light or by measuring changes in the ratio of intensities of two orthogonal states of polarization. These changes may also be observed by measuring the geometric distribution of the diffused or scattered light in two mutually orthogonal directions.

A hydrophobic agent or treatment may be applied on the anisotropic material (porous glass, polymer, etc.) to reduce sensitivity to water vapor while maintaining sensitivity to other chemicals. Specific surface treatments or surface chemistry may also be applied on the anisotropic material to change its surface energy or its affinity to specific chemicals.

BRIEF DESCRIPTION OF THE DRAWING

A detailed description of several preferred embodiments will be given herein below with reference to the following figures, in which like numbers refer to like elements:

FIGS. 12A through 15B are schematic diagrams showing several constructions of various disclosed sensors.

FIGS. 16A through 18B are schematic diagrams showing several implementations of an embedded sensor for use in air filtration or purification units.

FIG. 17 are schematic diagrams Showing the sensing element.

FIG. 18A-B are schematic diagrams showing an array of birefringent sensing elements.

DETAILED DESCRIPTION OF THE PREFERRED EMBODIMENTS

Figure 1:
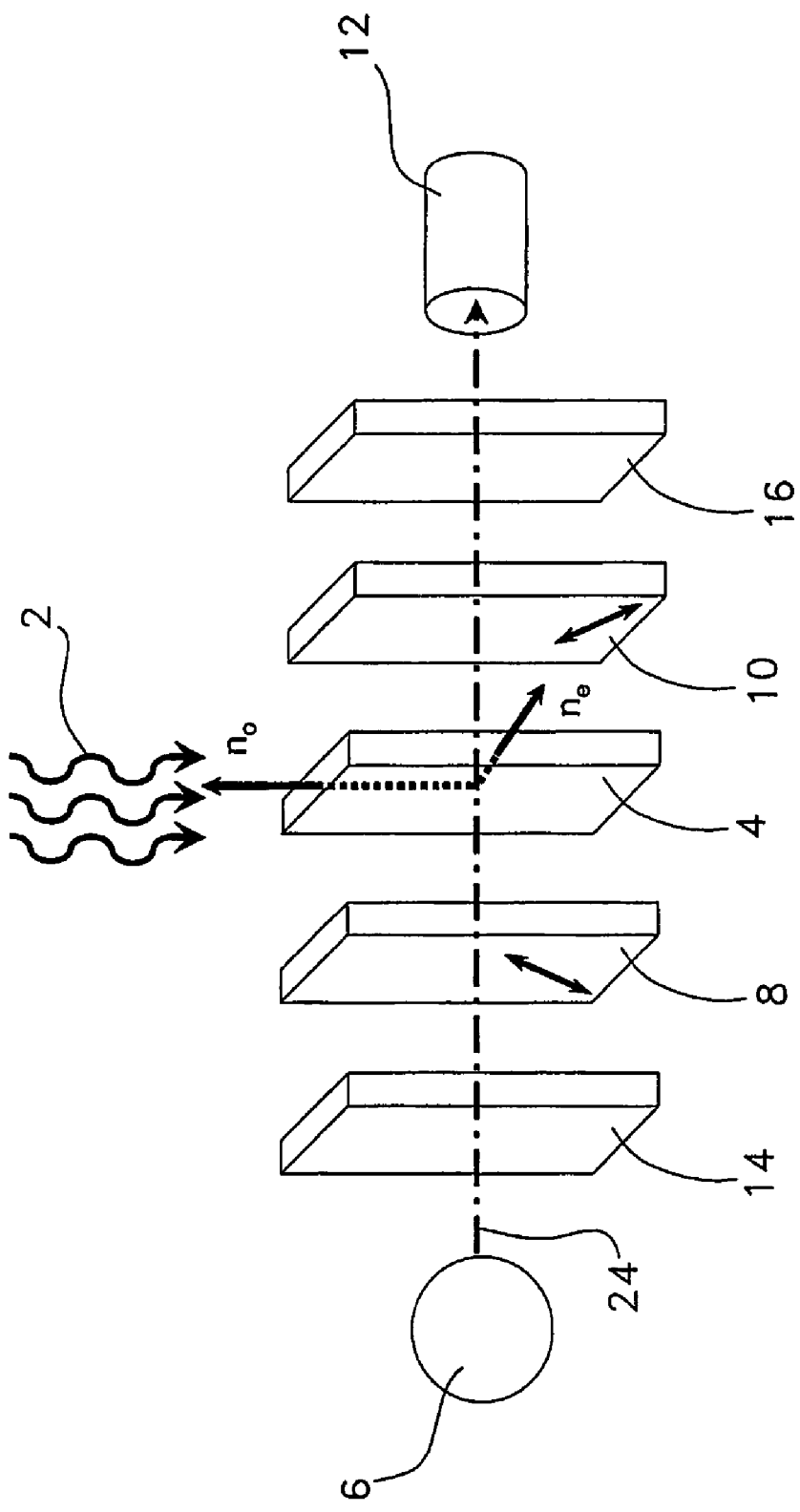
FIG. 1 is a schematic diagram showing an optical arrangement of a birefringence-based sensor.

As used in connection with this disclosure, the term "light" refers to electromagnetic radiation generally.

As used in connection with this disclosure, the expression "visible light" refers to light between 0.38 and 0.78 μm.

As used in connection with this disclosure, the expression "optical index" refers to a generally complex value containing a real and an imaginary component, with the real component corresponding to the refractive index for a material or volume of space and the imaginary component corresponding to the optical absorption coefficient for a material or volume of space.

As used in connection with this disclosure, the phrase "passing light through" when used with respect to a material refers to light that enters the material by refraction through a surface of incidence and propagates to a generally opposing surface where it exits the material by refraction.

As used in connection with this disclosure, the terms "transilluminate", "transillumination" and "transillumina-ting" when used with respect to an object refer to illumination of the object by passing light through its generally opposing walls.

As used in connection with this disclosure, the term "collecting" when used with respect to light refers to capturing light using an aperture, lens, goniometer, integrating sphere, human eye or other device that can sample or concentrate available light.

As used in connection with this disclosure, the term "detecting" when used with respect to light refers to characterizing or quantifying a property of light using visual observation, a sensor or device.

As used in connection with this disclosure, the term "anisotropic" when used with respect to a material refers to variation in a measured physical property depending upon the direction in the material along which the measurement is taken.

As used in connection with this disclosure, the expression "optical anisotropy" refers to variation in the measured refractive index or optical absorption coefficient for a material depending upon the direction in the material along which the measurement is taken.

As used in connection with this disclosure, the term "birefringence" refers to an anisotropic polarization state behavior for the real part of the optical index, generally manifested by the phase retardation of one polarization state relative to another polarization state in an incident beam.

As used in connection with this disclosure, the term "birefringent" when used with respect to a material refers to a material that selectively retards the phase of one polarization state relative to another polarization state in an incident beam.

As used in connection with this disclosure, the expression "optical dichroism" refers to an anisotropic absorption coefficient behavior for the imaginary part of the optical index, generally manifested by the selective absorption of one polarization state relative to another polarization state in an incident beam.

As used in connection with this disclosure, the term "dichroic" when used with respect to a material refers to a material that absorbs one polarization state more strongly than another polarization state in an incident beam.

Referring to FIG. 1, there is shown an optical arrangement of a sensor, for detecting a chemical substance in an analyte as depicted by arrows 2. The sensor has an anisotropic material 4 to be subjected to the analyte 2. Anisotropic material 4 acts as a chemical sensing element. The anisotropic material 4 may be a birefringent material placed between two linearly crossed polarizers 8, 10 which are between a light source 6 and a light detector 12. The chemical substance to be detected may be for example a solvent or any gas vapor or liquid whose presence could change the optical anisotropy of the sensing element.

The light source 6 provides light to be passed through the anisotropic material 4. The light source 6 may be a source of broadband light e.g. a white incandescent or halogen light, colored light as produced e.g. from a light emitting diode (LED) or from filtered light, or any kind of electromagnetic radiation in general. Emission line sources such as mercury, argon, sodium sources as well as laser sources may be used. Ambient light or daylight may also be used as the light source, depending on the intended application and the operating conditions of the sensor. Likewise, the light source 6 could be non-polarized or polarized. A filter 14 may be placed after the light source 6 to select or reject a range of wavelengths. Another filter 16 may be placed before the detector 12 to enhance the signal contrast or to cut unwanted wavelengths. The filters 14, 16 should be considered as optional elements in all subsequent figures.

The linear polarizer 8 may be of any type, e.g. a simple polarizing film such as Polaroid™ film, a multilayer polarizing film, polarizing cube beam splitters, etc. After passing through the polarizer 8, the light is linearly polarized.

The linear polarizer 10, similar to polarizer 8 acts as a linear analyzer.

The detector 12 may be a photoelectronic device or in certain cases simply a human eye as will be seen below.

Figure 2:
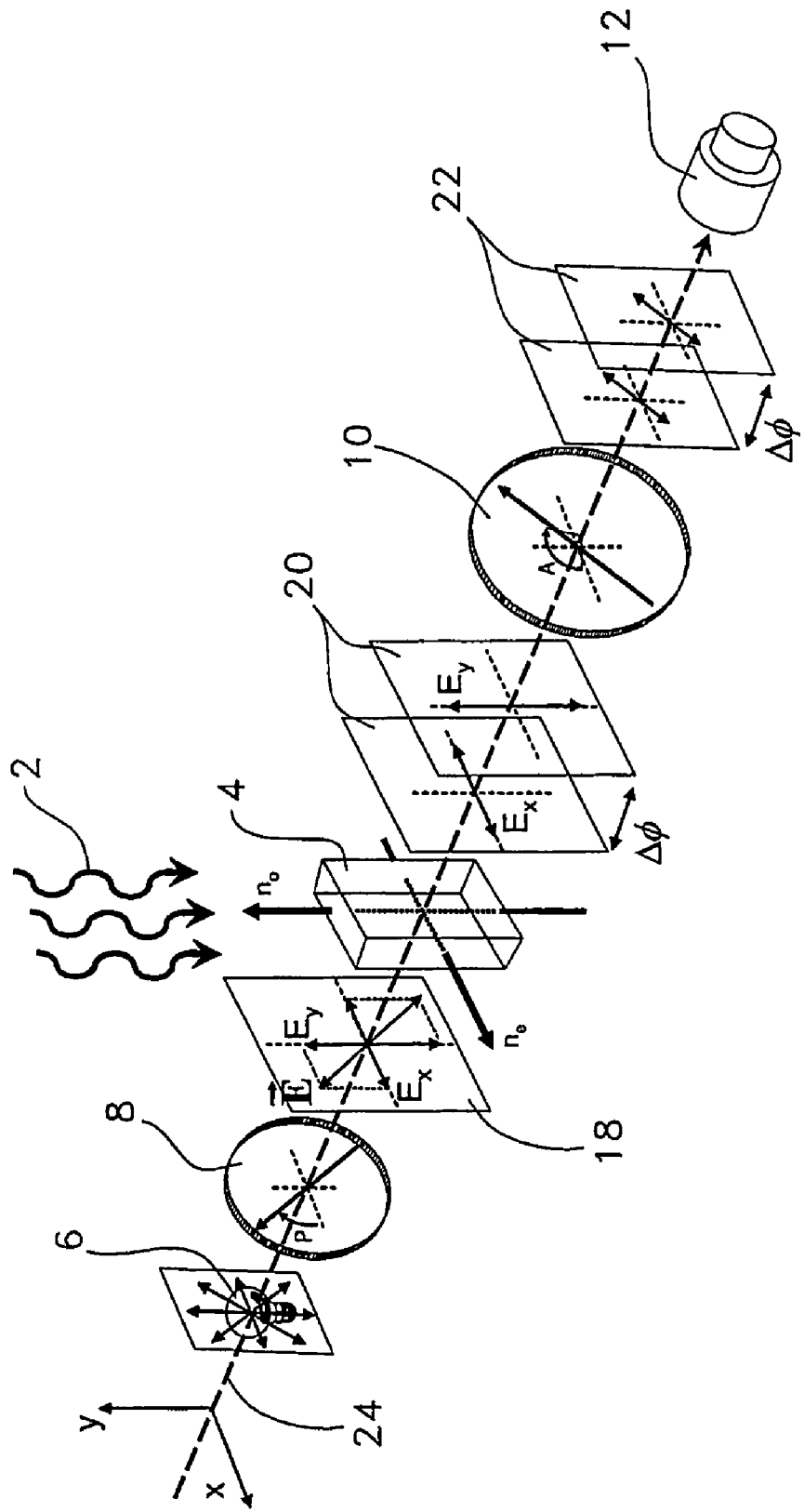
FIG. 2 is a schematic diagram showing optical effects in a birefringence-based sensor.

Referring to FIG. 2, the optical axis of the birefringent material 4 is placed in the propagation plane (normal to the propagation axis 24) preferably at 45° with respect to the linear polarization direction. The electrical field vector $\vec{E}$ of linear polarized light is decomposed in two orthogonal projections $E_x$, $E_y$ along the ordinary $n_o$ and extraordinary $n_e$ refractive indices, as depicted in diagram 18. Due to birefringence, each projection of the electrical field vector experiences a different refractive index and thus a different light path resulting in a phase shift $\Delta\phi$ between the two projected components of the electric field vector as depicted in diagram 20. At a given wavelength $\lambda$, the phase shift $\Delta\phi$ is given by:

$$\Delta\phi = \frac{2\pi \cdot d \cdot \Delta n}{\lambda} \tag{1}$$

where d is the thickness of the birefringent sample 4 and $\Delta n = n_e - n_o$ is the birefringence.

The linear analyzer 10 is preferably crossed (e.g., at 90°) with the polarizer 8 to make sure that the only light passing through the analyzer 10 is light that has been rotated by the birefringent sample 4. The analyzer 10 transmits along its axis of polarization the components of the two phase shifted projected electrical field vectors that experienced different optical paths, as depicted in diagram 22.

The detector 12 may be simply a naked eye, an imaging system with a CCD camera (not shown), a spectrophotometer (not shown), or just a photodiode (not shown). For a uniaxially birefringent material, the output intensity $I_{out\perp}$ for 90° crossed polarizers at a given wavelength $\lambda$ is given by:

$$I_{out\perp} = \kappa \cdot \frac{I_{source}}{2} \cdot \sin^2\left(\frac{\pi}{\lambda} \cdot d \cdot \Delta n\right) \tag{2}$$

where $\kappa$ is a positive factor ($\leq 1$) that takes into account all the power losses such as partial reflections and possible diffusion along the optical path 24, $I_{source}$ is the source intensity, d is the thickness of the birefringent material and $\Delta n = n_e - n_o$ is the birefringence.

In such conditions, maxima of transmission occur when:

$$d \cdot |\Delta n| = \frac{2m+1}{2} \cdot \lambda \tag{3}$$

where m=0, 1, 2, . . . , and minima of transmission occur when:

$$d \cdot |\Delta n| = m \cdot \lambda \tag{4}$$

Figure 9:
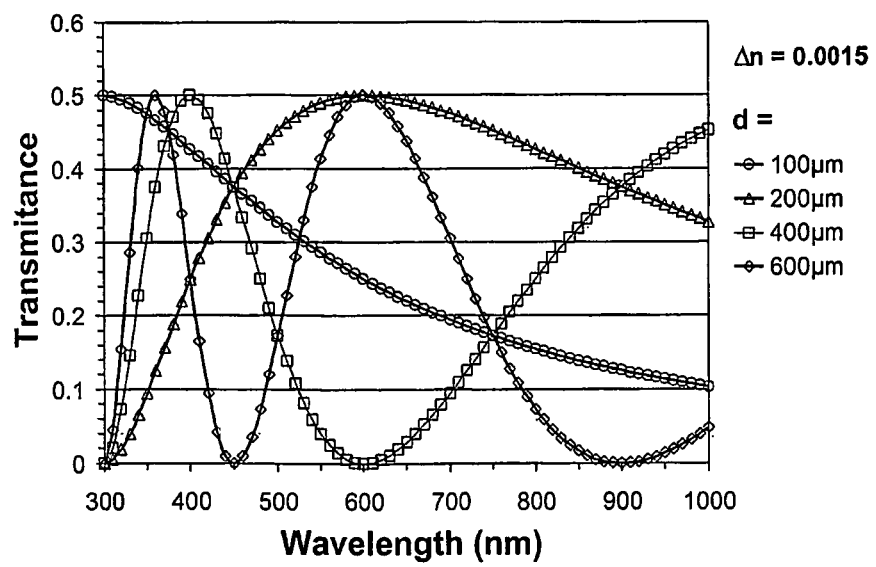
FIGS. 9-11 are graphs showing respectively effects of birefringent material thickness, of variable birefringence, and of polarizer orientation in various disclosed sensors.
Figure 10:
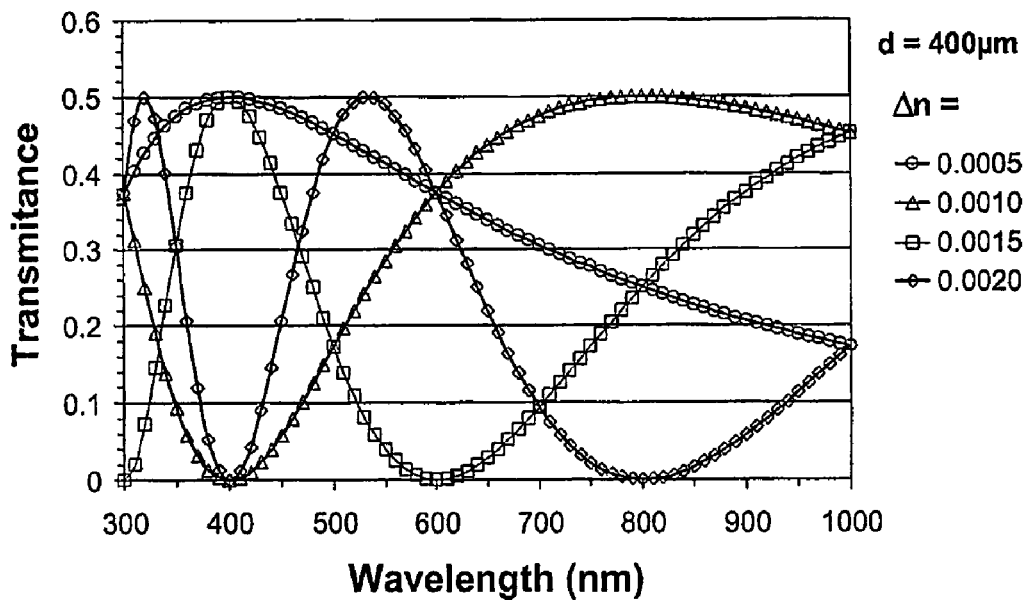

The transmittance spectrum depends thus on the thickness d as well as on the birefringence $\Delta n$ of the anisotropic material 4 as shown in the graphs presented in FIGS. 9 and 10 respectively.

Referring to FIG. 9, there is shown the effect of increasing thickness for a given birefringence.

Referring to FIG. 10, there is shown the effect of increasing birefringence for a given thickness.

Figure 11:
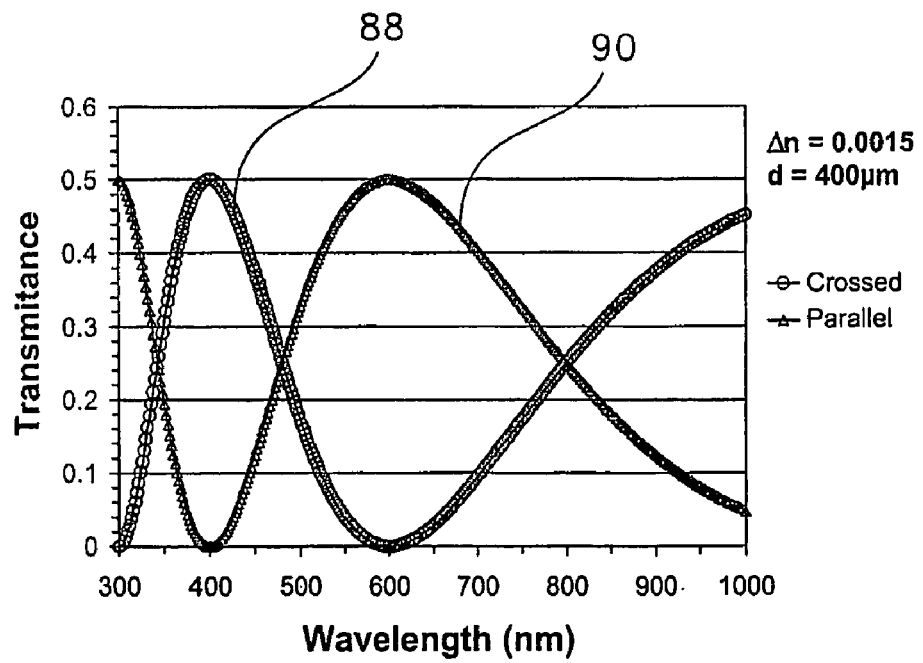

Referring to FIG. 11, there is shown the theoretical transmittance calculated in the wavelength range of $\lambda$=300 nm to $\lambda$=1000 nm for an optical birefringent material ($\Delta n$=0.0015) and a constant thickness d=400 μm placed at 45° between ideal crossed and parallel polarizers as depicted by curves 88, 90 respectively.

The higher the thickness or absolute value of the birefringence, the more maxima and minima are present in the transmittance spectra.

When the presence of a chemical substance affects the birefringence or the thickness of the anisotropic material, the phase shift $\Delta\phi$ changes and is detected by the detector 12, either by a change in intensity at a given wavelength or given wavelengths, or by a change in the transmitted spectrum. The change may be measured for example using a spectrophotometer or interpreted by noting a change in the transmitted color.

Improved sensitivity may be achieved with crossed (e.g., at 90°) polarizer 8 and analyzer 10 and with a birefringent material 4 with its optical axis placed at 45° relative to the linear polarization axis, but angular precision need not be strictly observed and a tolerance in these angles, e.g. ±10°, may be acceptable.

An advantage of the FIG. 1 arrangement is that the only light that is detected is light that has been shifted by the birefringent material 4, since other light from the source 6 would be stopped by the crossed analyzer 10. This can provide much better sensitivity than is obtained when the polarizers are omitted and transmission intensity alone is measured.

The polarizer 8 and the analyzer 10 may also have parallel optical axes. In such configuration, at a given wavelength $\lambda$, the output intensity $I_{out//}$ is now given by:

$$I_{out//} = \kappa \cdot \frac{I_{source}}{2} \cdot \cos^2\left(\frac{\pi}{\lambda} \cdot d \cdot \Delta n\right) \tag{5}$$

In that case, the transmitted spectrum of the sensing element is inverted compared to the configuration with crossed polarizer 8 and analyzer 10. Therefore, the former maxima of transmission now correspond to minima of transmission and vice versa. The inversion of the transmitted spectrum may be an advantage offering an alternative for the selection of appropriate wavelengths for light detection when the birefringent parameters cannot be easily controlled. A disadvantage of this configuration is that the detector 12 may detect light that does not pass through the anisotropic material 4 (such as reflected light) whereas such light would be blocked in the previous configuration. The alignment of the light source 6, the birefringent material 4 and the light detector 12 may need to be more carefully controlled in the parallel configuration.

Figure 3:
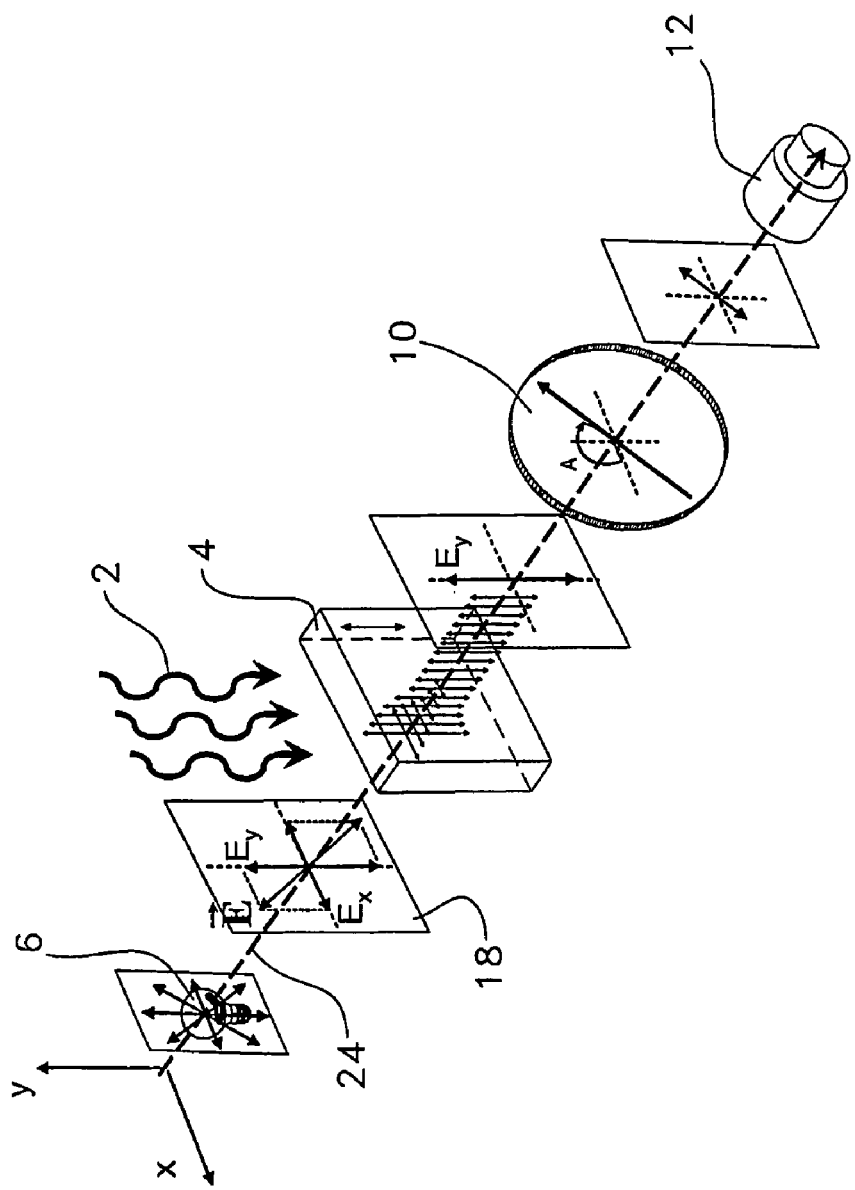
FIG. 3 is a schematic diagram showing optical effects in a dichroism-based sensor.

Referring to FIG. 3, dichroism or anisotropic diffusion may be used instead of birefringence for detecting the chemical substance in the analyte 2. The presence of a chemical could affect the dichroism or anisotropic diffusion of the material 4, modifying the light transmitted by the analyzer 10 as detected by the detector 12. In fact, a variety of parameters reflecting a change of the optical anisotropy of the material 4 may be used provided that an appropriate optical arrangement is available.

Figure 4:
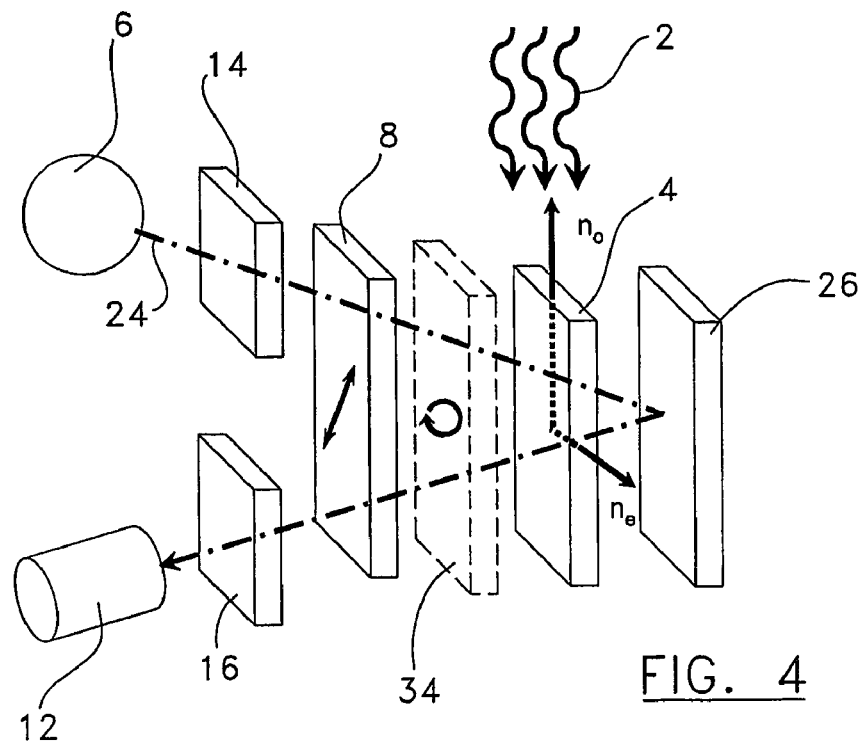
FIGS. 4-7 are schematic diagrams showing several possible reflective optical arrangements of a birefringence-based sensor.

Referring to FIG. 4 and considering only solid line elements, only one polarizer 8 and a mirror 26 may be used in a reflective configuration. The isotropic light of the source 6 then passes through the linear polarizer 8 and the polarized light passes through the birefringent material 4 whose optical axis is preferably placed at 45° with respect to the polarization axis, producing a phase shift as described above. The light is then reflected on the mirror 26 which may be independent from the anisotropic material 4 or advantageously be a metal deposition (such as chromium) or a reflecting multilayer structure directly positioned on one surface of the birefringent material 4 and sufficiently thick for a good reflection in order to reduce power losses at small angles of incidence. The reflection does not significantly change the polarization state of the incident light at small incident angles and only the direction of light propagation is changed. After reflection, the light again passes through the birefringent material 4 with an additional effect on the phase shift which is doubled. The light is recombined on the polarizer 8 which plays the role of a parallel analyzer, and the resulting light is finally measured by the detector 12.

An advantage of this configuration is that no alignment of the polarizer and analyzer is necessary since the polarizer and the analyzer are indeed the same device and thus intrinsically already parallel. Another advantage is that the light crosses twice the thickness of the anisotropic material 4, doubling thus the effect of anisotropic light propagation without doubling the real thickness of the detecting element. This is very useful in order to increase the kinetics of sensor response since, for the same effect as with the transmission mode shown in FIG. 1 (but with parallel polarizers), the chemical substance has only to diffuse inside half of the anisotropic material, keeping in mind that diffusion may be a slow process.

Figure 5:
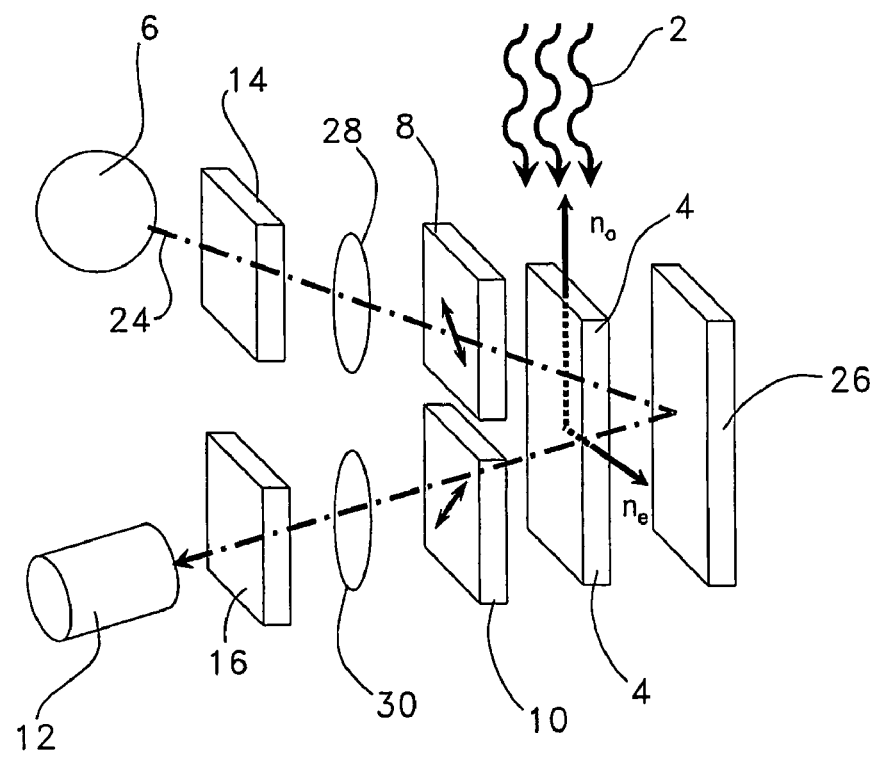

Referring to FIG. 5, a separate crossed analyzer 10 may be used for detection of the light shifted only by the birefringent material 4, with the possible drawback that it may be difficult to bring the crossed polarizer 8 and analyzer 10 sufficiently close together when miniaturization of the sensor is desired. In this case, the use of focusing optical lenses 28, 30 may be helpful. Such a difficulty could also be overcome using other designs techniques that will be familiar to those skilled in the art.

Figure 6:
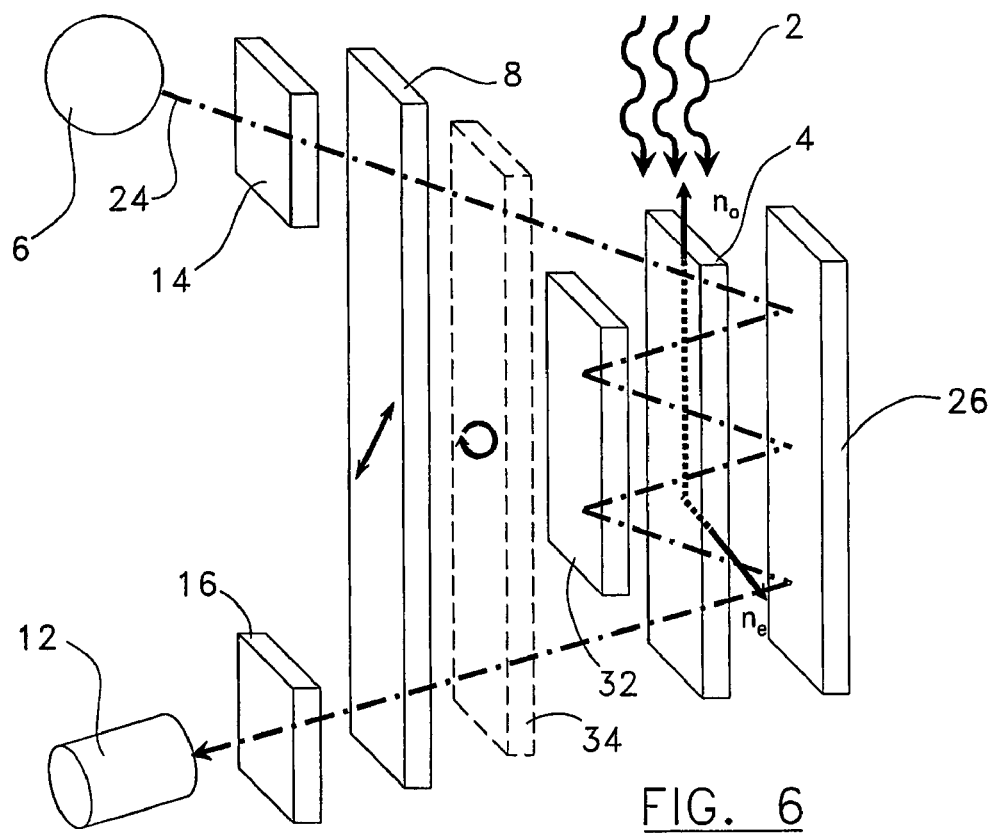

In general, the optical path length through the anisotropic material can vary widely, e.g., from about $10^{-7}$ meters to about $10^{-2}$ meters. Referring to FIG. 6 and considering only solid line elements, a small extra mirror 32 may be positioned preferably in parallel with the first mirror 26 to enable multiple reflections and increased optical path length through the anisotropic material 4 before detection. In this configuration, the light source 6 is preferably collimated (or has a reduced angle profile such as for instance obtained at the output of an optical fiber) and has a known incident angle in order to control the number of reflections inside the anisotropic material 4 and thus the optical path 24. Additional focusing optical lenses or other designs could be used if necessary as mentioned for FIG. 5. The number of reflections is also dependant on the distance between the two parallel mirrors 26, 32 which could be adjusted in order to obtain an optimum number of reflections. The second mirror 32 may advantageously be a metal deposition (such as chromium) or a reflecting multilayer structure patterned directly onto the surface of the polarizer 8 and sufficiently thick for good reflection in order to reduce power losses.

Figure 7:
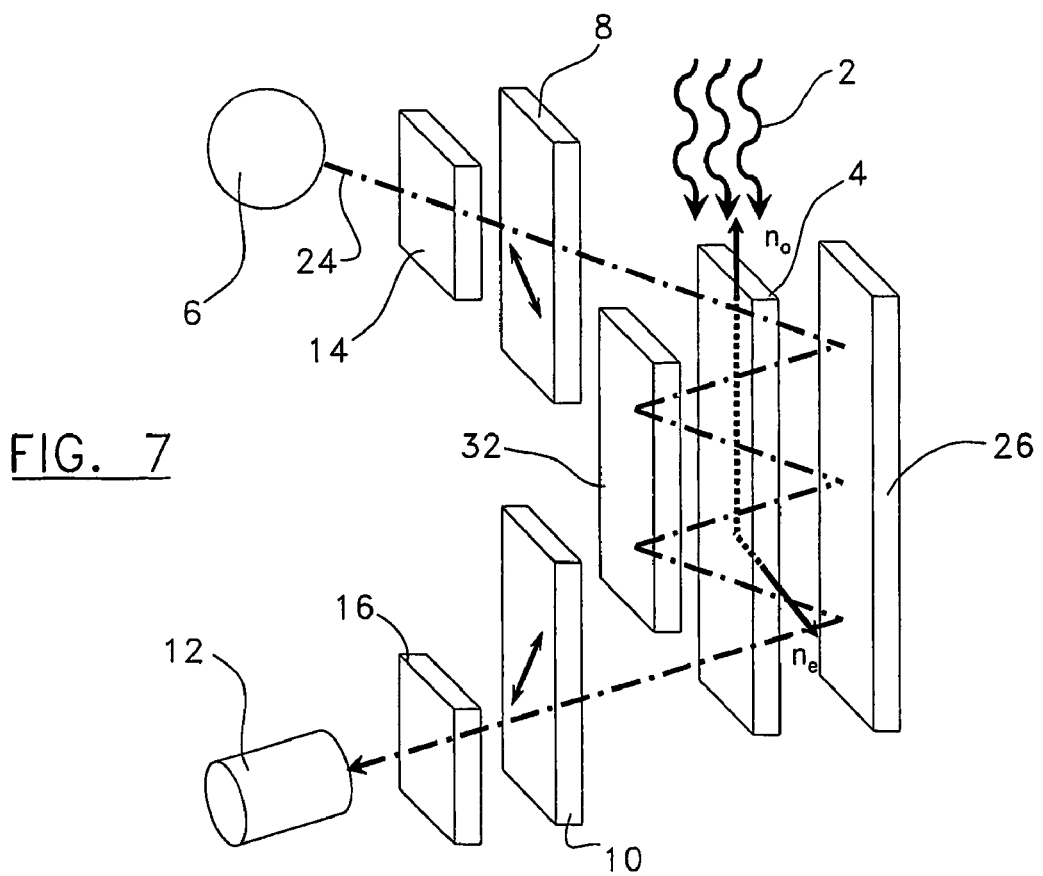

Referring to FIG. 7, if the physical dimension of the sensing element is large enough, a crossed analyzer 10 may be placed before the detector 12 to cut all the light coming from outside the anisotropic material 4 (e.g. unwanted reflections). In such a configuration, the light will be guided on a short path between the two mirrors 26, 32 to maximize the optical length through the anisotropic material 4. Again additional focusing optical lenses or other designs could be used if necessary as mentioned for FIG. 5.

An advantage of these multiple reflective configurations is that better sensitivity may be obtained without sacrificing the response time of the sensor due to slow diffusion of chemicals through a possibly thick sensing material 4. In this configuration, low birefringent materials may also be used and better sensitivity to swelling or shrinking of anisotropic materials in the presence of chemicals may be achieved in that detection of changes in the optical path may be more accurate than detection of other properties.

Referring back to FIGS. 4 and 6 but considering also the dashed element, an extra retarding plate 34 (preferably a one-quarter wave retarder) may be used right after the linear polarizer 8. These two optical elements are usually combined and known as a circular polarizer. The light passing through such an optical arrangement becomes circularly polarized. If there is no anisotropic material, light returns after one reflection (or an odd number of reflections) to the circular polarizer 8, 34 with a different polarization state and is then blocked because after going through the one-quarter wave retarder, it becomes linearly polarized again but with a new orientation at 90° to the transmission axis of the polarizer 8. When an optical anisotropic material 4 is introduced between the circular polarizer 8, 34 and the mirror 26, an extra phase shift is introduced and some light may thus be detected accordingly.

An advantage of such a configuration is that only the light passing through the optical anisotropic material 4 is detected, as in the case with crossed linear polarizers 8, 10, but without the necessity to cross the polarizers carefully. Another advantage is that the light passes at least twice through the anisotropic material 4, thus at least doubling the effect of anisotropic light propagation without doubling the real thickness of the detecting element, giving better kinetic performance. However since commercially available circular polarizers induce quite a lot of attenuation, an intense light source may be required for best performance.

Figure 8:
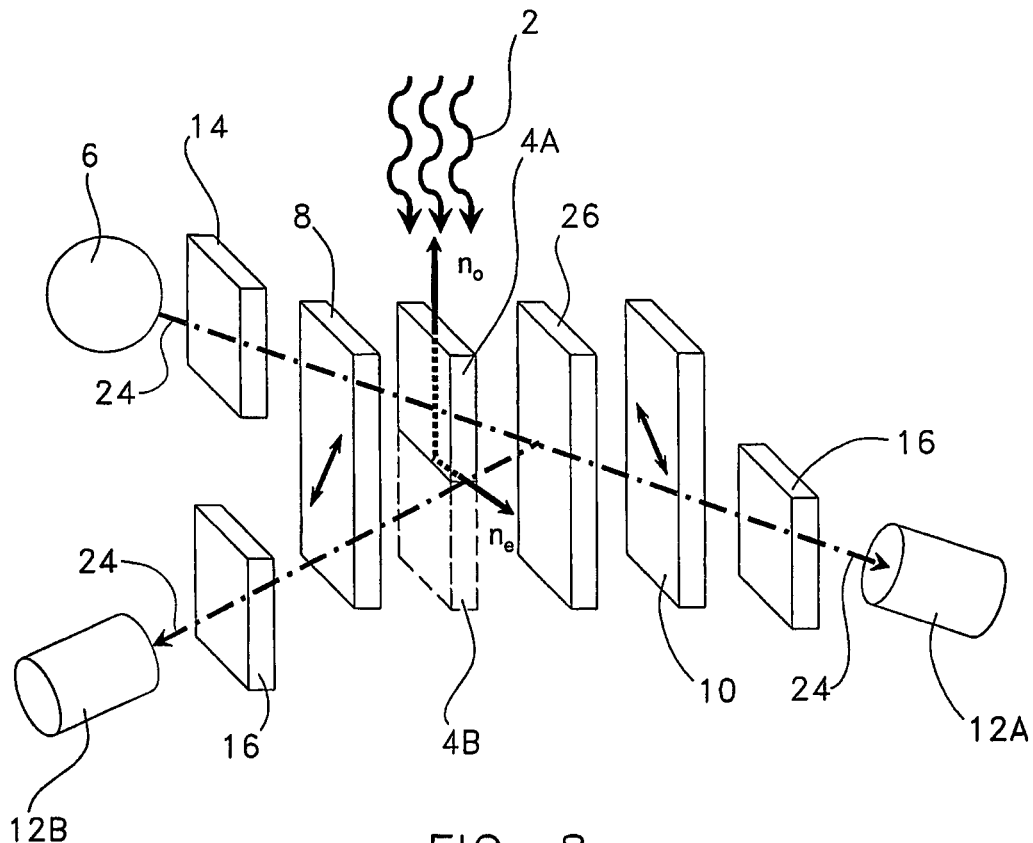
FIG. 8 is schematic diagrams showing several possible semi-reflective optical arrangements of a birefringence-based sensor.

Referring to FIG. 8, where extreme sensitivity is necessary the above-mentioned transmitting and reflective configurations may be combined. The light source 6 is preferably narrow band, and two detectors 12A-B are employed. The mirror 26 is partially reflective. The input light is linearly polarized before passing through the birefringent material 4A whose optical axis is placed preferably at 45° with respect to the polarization axis, inducing a phase shift $\Delta\phi$. Then the light hits the partially reflective mirror 26 and is separated into two rays. The ratio of the intensity of the two rays may be controlled for example by the characteristics of the partially reflective mirror or by the position of the two detectors 12A-

B. The partially reflective mirror 26 may advantageously be a semi-reflective coating directly deposited onto the perpendicular analyzer 10 or onto the anisotropic material 4A-B. The arrangement may be such that the reflected ray passes through the birefringent material 4B again or not and experiences an additional similar effect on the phase shift $\Delta\phi$ or not before passing through the parallel analyzer 8 and being collected by the detector 12B: which measures the parallel intensity $I_{out//}$. The transmitted ray passes through the perpendicular analyzer 10 before being collected by the other detector 12A which measures the perpendicular intensity $I_{out\perp}$. In this configuration, the detectors 12A-B preferably are electronic detectors such as photodiodes producing currents proportional to the measured light intensities. As mentioned above, for the same thickness of birefringent material 4A-B, the perpendicular intensity $I_{out\perp}$ and the parallel intensity $I_{out//}$ are inverted (e.g. in the spectral plane, a minimum of one is a maximum for the other and vice versa). In the case where the reflected light passes in the birefringent material 4B, the optical thickness for $I_{out//}$ is double that of $I_{out\perp}$, which means a doubled periodicity in $1/\lambda$. For that case, the maxima and minima of $I_{out\perp}$ correspond however to maxima of $I_{out//}$, and minima of $I_{out//}$ correspond to half of the maximum of $I_{out\perp}$. Thus better sensitivity may be achieved by following e.g. the ratio $I_{out//}/I_{out\perp}$ during the contact with the chemical substance. Since the minimum of $I_{out\perp}$ is theoretically zero, the ratio $I_{out//}/I_{out\perp}$ diverges to the infinite at each minimum of $I_{out\perp}$. Experimentally, this is not the case but each time $I_{out\perp}$ is close to its minimum, the ratio $I_{out//}/I_{out\perp}$ increases dramatically and this ratio also decreases rapidly to zero or to a small value outside of the minima of $I_{out\perp}$. The ratio $I_{out//}/I_{out\perp}$ as a function of $\lambda$ (or $1/\lambda$) has peaks positioned at each minima of $I_{out\perp}$, that is when $d\cdot|\Delta n|=m\cdot\lambda$, where m is a positive integer. It is thus possible to select the position of the peak ratio maxima either by changing the birefringence $\Delta n$ of the anisotropic material 4, or more simply by changing its thickness d. For instance, for a birefringence of $\Delta n=1.5\cdot10^{-3}$, a thickness of $d\approx420$ μm would be necessary to have the first order peak maximum (m=1) in the red at 630 nm (the second order, m=2, would be in the UV region at ~315 nm).

This property may be used to increase drastically the sensitivity of the sensor as compared to single intensity measurements possibly by a factor of at least three orders of magnitude. The sensitivity will depend on the slope of the $I_{out//}/I_{out\perp}$ ratio as a function of $\lambda$ (or $1/\lambda$) which may be tuned for instance by selecting the reflectivity of the partially reflective mirror 26.

The inverse ratio $I_{out\perp}/I_{out//}$ may also be used if desired.

One great advantage of such a configuration is that since an intensity ratio is calculated, this parameter is not sensitive to possible fluctuations of the light source 6 (e.g. due to aging).

Preferably, the light source 6 is a narrow band light source with its peak of emission corresponding to the minimum of $I_{out\perp}$ without any chemical substance (e.g., to the peak of the $I_{out//}/I_{out\perp}$ ratio), and the two detectors 12A-B have their peak of detection at the same position. Thus, without any chemical substance to be detected, the measured $I_{out//}/I_{out\perp}$ ratio would be maximum. A small change in the birefringence due to the presence of a chemical substance would lead to a rapid decrease of the ratio by several orders of magnitude. Using the above example values, a decrease of birefringence as small as $10^{-4}$ would shift the peak of the ratio from 630 nm down to about 590 nm which would lead to a decrease of the ratio down to almost zero, indicating the presence of the chemical substance to be detected.

Figure 12B:
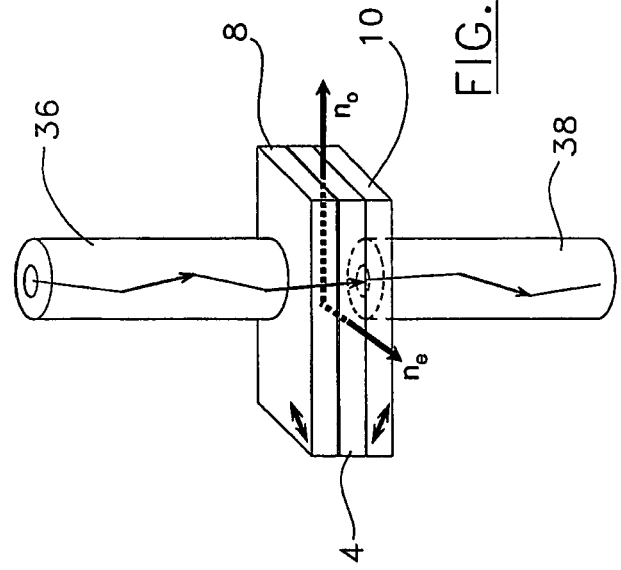
Figure 12A:
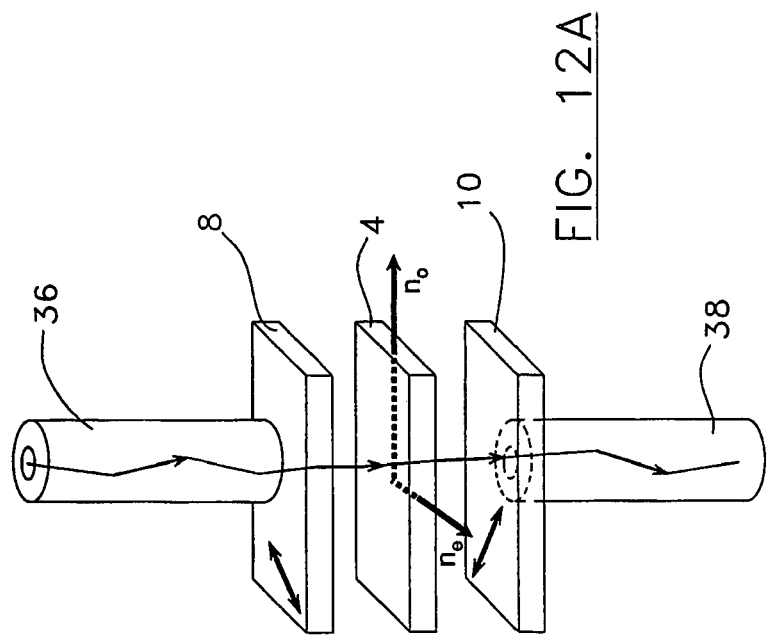
Figure 12C:
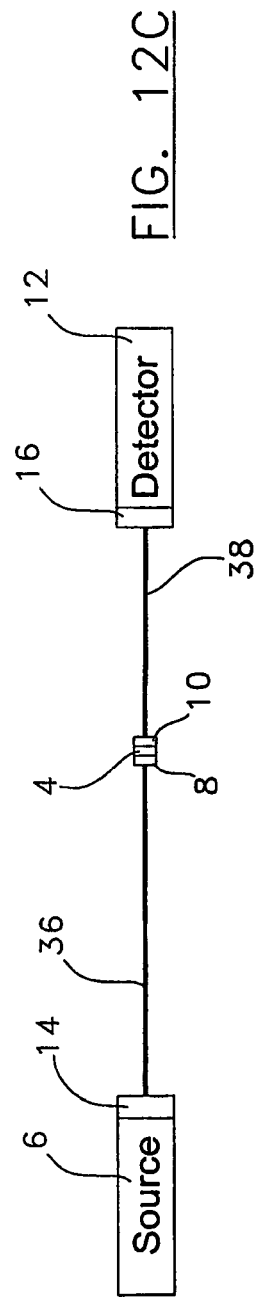

Referring to FIGS. 12A-C, the light produced by the light source 6 may be guided to the anisotropic material 4 and collected to be guided to the detector 12 using any type of optical fibers 36, 38, including polarization maintaining fibers, but preferably multimode optical fibers. Any optical waveguide such as inexpensive light pipe could also be used if desired. The anisotropic material 4 may for example be a transilluminated birefringent porous fiber or slab. Polarization maintaining fibers may be used to avoid placing the polarizers 8, 10 directly on both sides of the porous fiber 4, with the drawback that they are presently relatively expensive and their use would complicate the positioning of the sensing element since it would be necessary to know their orientation with respect to the birefringent porous fiber 4.

The optical fiber 36 may be conveniently terminated with the polarizer 8 such as a Polaroid™ film or a linearly polarizing multilayer coating. After passing through the anisotropic material 4 placed at for instance at ~45° with respect to the polarization axis, the light is collected by the similar optical fiber 38 with the analyzer 10 crossed or parallel to the first polarizer 8. In order to hold all the parts together in the proper orientation, the optical fibers 36, 38 mounted with the polarizers 8, 10 and the birefringent material 4 could be assembled (e.g., as an integral unit in which the polarizer and analyzer contact and optionally are adhered to the anisotropic material) inside a perforated or permeable tube (not shown) that still allows the contact of the chemical substance with the anisotropic material 4. An advantage of this design is that the permeable tube could be used to give a certain selectivity to the sensor that could thus only detect the analyte coming across the tube. Another advantage of such a design is that a small size sensor may be placed into an environment where light is difficult to bring such as a closed respiratory cartridge 40 (as shown in FIGS. 16A-B) filled for instance with activated carbon 42.

Figure 16B:
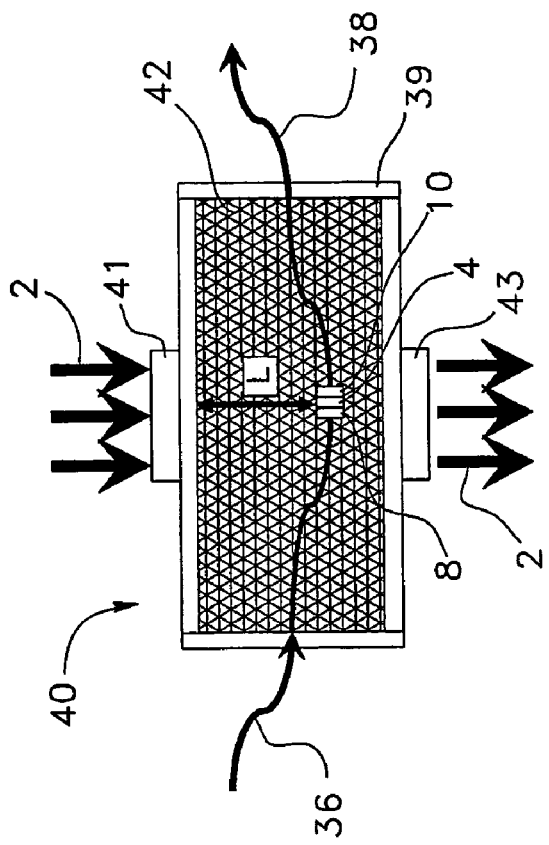
Figure 16A:
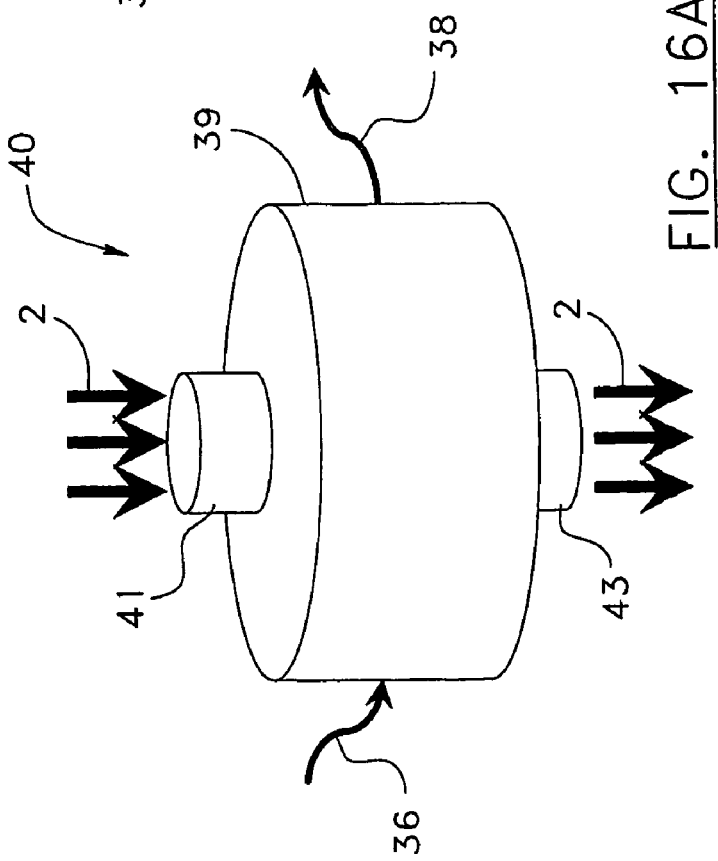

Referring to FIGS. 16A-B, the sensor may thus be embedded and used as an end-of-service-life indicator for the cartridge 40. Cartridge 40 has housing 39, inlet 41 and outlet 43. A flow is established between the inlet 41 and the outlet 43 through sorbent bed 42 (made, for example, from activated carbon, alumina granules or other particulate materials having an affinity for the desired chemical substance). Sorbent bed 42 traps chemicals creating a concentration gradient of such chemicals according to the flow direction. The detector signal changes when chemicals such as organic vapors reach the sensing element formed by the anisotropic material 4 indicating that the sorbent 42 is full. The position L (see on FIG. 16B) of the sensor inside the carbon bed 42 should be chosen to allow a secure unused sorbent reserve (e.g. a 10% remaining life as specified by NIOSH standards).

The embedded sensors of the invention may also be employed in dosimeters that indicate or measure the overall exposure of a person or an enclosed or semi-enclosed area to a chemical substance of interest. The dosimeter typically will include a housing surrounding an absorbent bed in which the sensor is embedded. The housing may be permeable to the desired chemical substance or may include one or more apertures that permit the desired chemical substance to diffuse into the bed. The cartridge 40 could be modified for such use by, for example, perforating the housing 39, or by enlarging the inlet 41 and outlet 43, or both. If the housing 39 is suitably perforated then the inlet 41 or outlet 43 could if desired be eliminated or used instead as a simple aperture permitting the desired chemical substance to diffuse into the bed. The housing should be properly designed to promote access of the analyte 2 to the sorbent bed (e.g. with a wider aperture or multiple apertures). The housing may be made for example from plastic, glass, metal or other suitable materials. The absorbent bed may be made for example from activated carbon, alumina granules or other particulate materials having an affinity for the desired chemical substance. The bed can if desired be made using bonded granules, e.g. bonded carbon granules, or a flexible web containing absorbent granules, e.g. absorbent carbon granules. Desirably the absorbent bed retains the desired substance sufficiently strongly so that when the concentration of the desired chemical substance decreases from peak levels the substance will largely remain within the housing rather than being released into the surrounding atmosphere. Typically the sensor may be located at or near the center of the bed or along an impermeable portion of the housing wall. Although a flowing air stream may be used to introduce an analyte into the bed, typically the dosimeter will be constructed so that the desired chemical substance diffuses into the housing rather than passing through the housing as is the case for a respiratory protection filter cartridge. A suitable optical waveguide may be employed to conduct light into and out of the sensor (as described in FIGS. 16A-B), or the housing may be equipped with a suitable transparent window or wall (as later described on FIG. 18A-B). Other designs (such as the one later described on FIG. 17) are also possible. The housing may be designed to be wearable by the user (e.g., as a badge, medallion, wristband or other article designed to be worn on or about the body), may be mounted in or near an area for which dosimeter detection is required (e.g. as a wall-mounted or ventilation duct-mounted device in public gathering places such as train or subway stations, airports, auditoriums and the like) or may be mounted on a suitable mobile measuring unit (e.g. a van, aircraft, ship or other vehicle) for use in monitoring larger areas. U.S. Patent No. 4,597,942 (Meathrel), U.S. Pat. No. 5,206,118 (Sidney et al.), U.S. Pat. No. 5,659,296 (Debe et al.), U.S. Pat. No. 6,031,454 (Lovejoy et al.), U.S. Pat. No. 6,432,721 B1 (Zook et al.) and U.S. Pat. No. 6,610,977 B2 (Megerle) describe representative dosimeter devices or housings that may be adapted for use with sensors of the invention to indicate or measure exposure to a chemical substance of interest.

Using an anisotropic sensor embedded inside a sorbent material could increase the sensitivity of the sensor since the product to be detected may be concentrated inside the sorbent material enabling possible transfer to the anisotropic sensor due to proximity of the two. For instance, birefringent porous glass used as anisotropic material will be more sensitive to toluene when the sensor is embedded inside activated porous carbon.

Figure 13A:
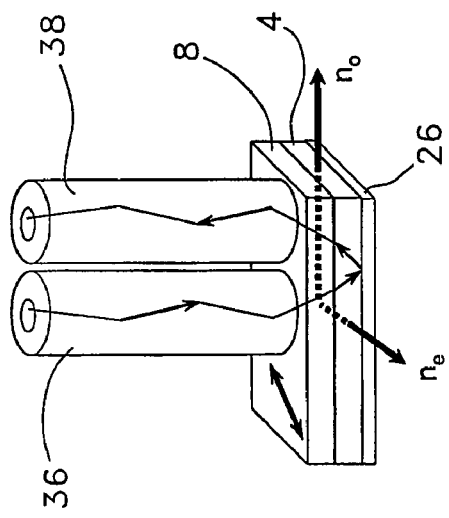
Figure 13B:
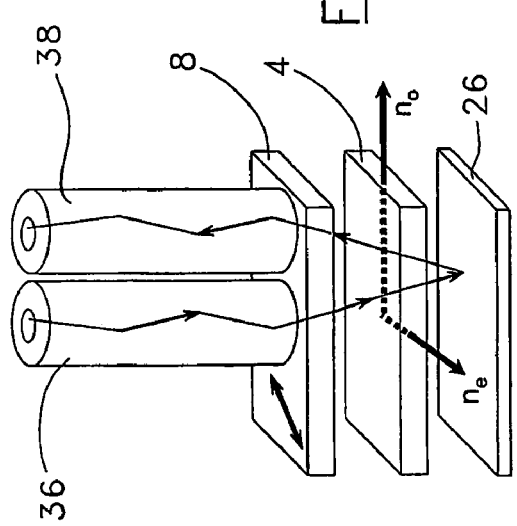
Figure 13C:
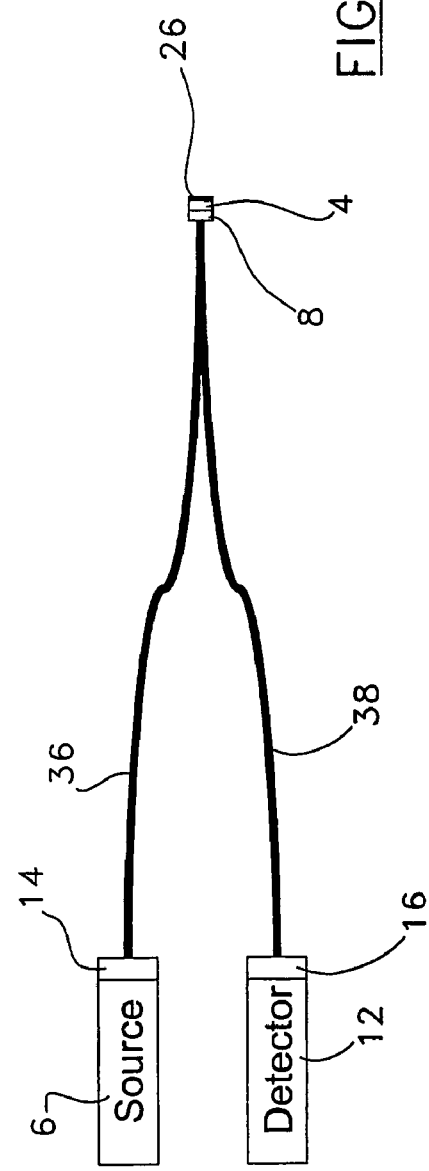

Referring to FIGS. 13A-C, there is shown an implementation of a sensor in a reflective configuration in order to have the input and the output optical fibers 36, 38 placed on the same side of the anisotropic material 4. The distance or angle between the axis of the two optical fibers 36, 38 and the distance from their termination surfaces to the mirror 26 should be adapted to the numerical aperture of the fibers 36, 38 in order to collect sufficient light for detection.

Referring to FIGS. 14A-B, there is shown an implementation of a sensor in a semi-reflective configuration, which may be used if better sensitivity is desired or required. In such a case, three optical fibers 36, 38 and 44 are needed: one 36 to bring the light to the anisotropic material 4, another 38 to collect the reflected light and a third 44 to collect the transmitted light. In that configuration, the polarizer 8 and the analyzer 10 are preferably crossed. Using the signal from the two output fibers 38, 44, the ratio of the parallel and perpendicular intensities can then be calculated for better sensitivity as already explained hereinabove.

Figure 15A:
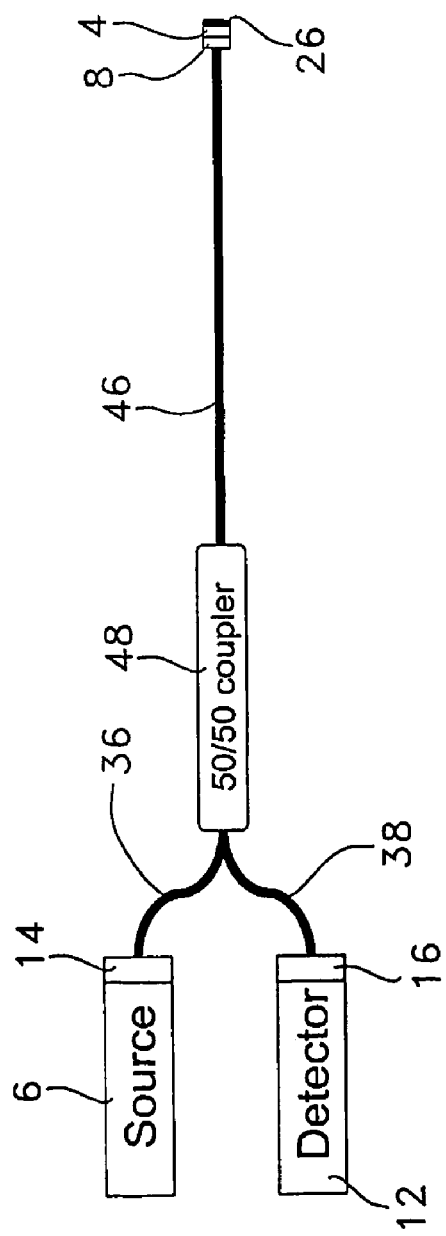
Figure 15B:
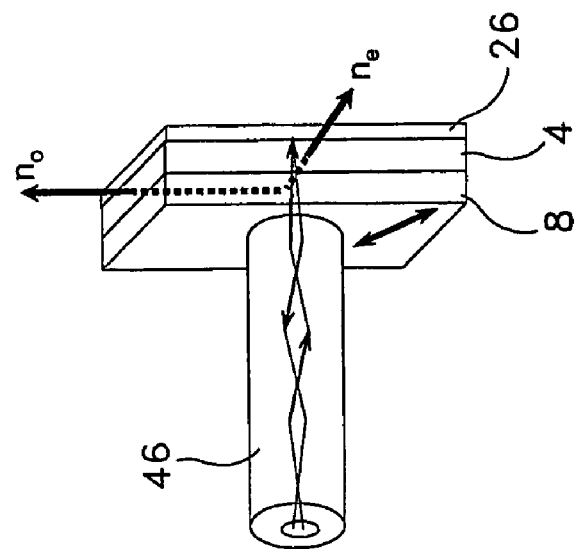

Referring to FIGS. 15A-B, for applications where the size of the optical fiber is important, an arrangement using a single optical fiber 46 with a sensing element mounted in reflection mode (with only one polarizer 8 which could be linear or circular polarizer, a birefringent material 4 placed preferably at 45° with respect to the polarization axis and a mirror 26) may be coupled to the light source 6 and the detector 12 by a 50/50 light coupler 48 (or beam splitter). The optical fiber may advantageously be polished with an angle (e.g. 8° with respect to the surface normal) in order to reduce the light directly reflecting on the extremity without exiting the optical fiber. This arrangement is more expensive and requires generally a more powerful light source 6 since the 50/50 light coupler 48 theoretically divides the power transmitted from the source 6 to the detector 12 by four. The ratio of the light coupler 48 may be different from 50/50 if desired.

Figure 17:
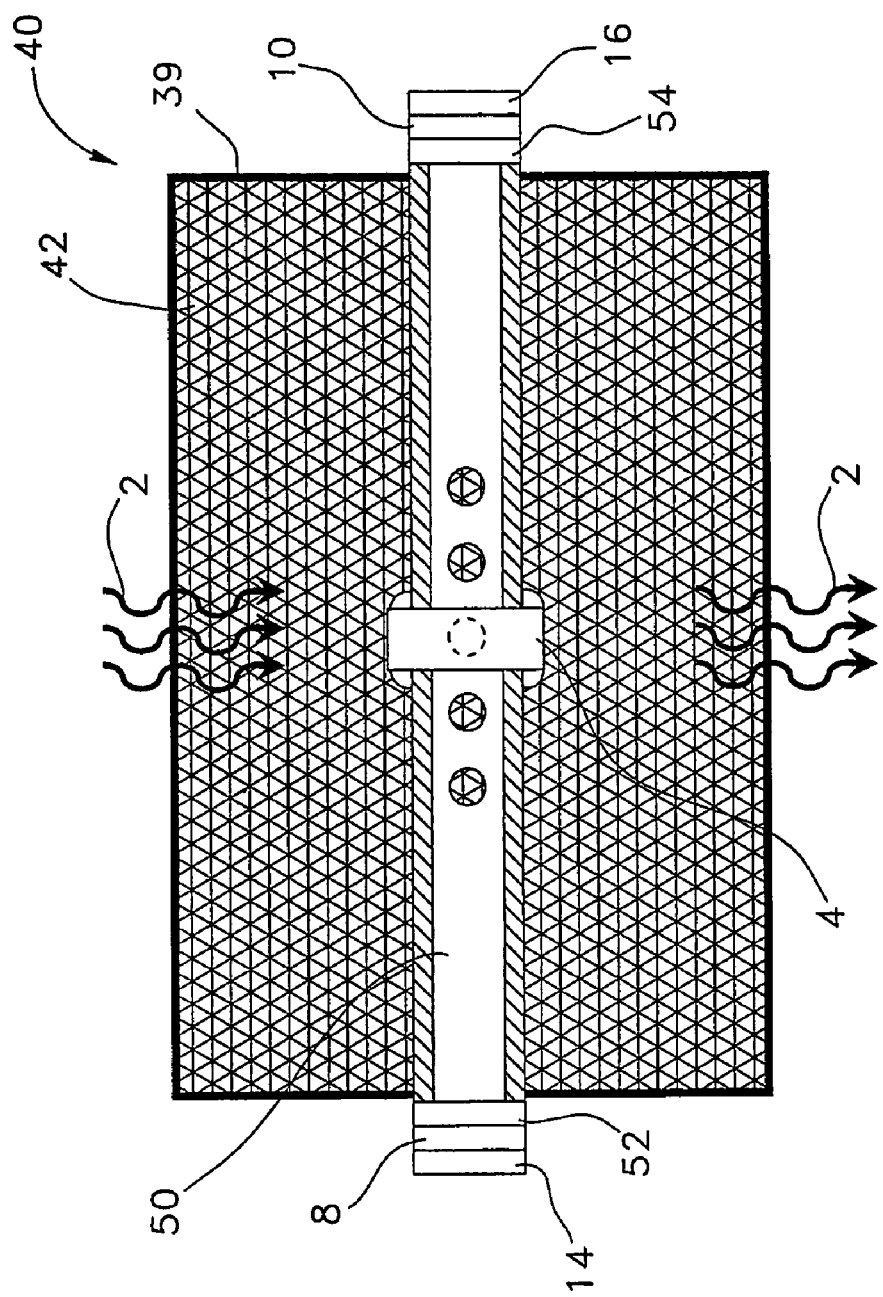

Referring to FIG. 17, the sensing element may be included inside a perforated or permeable tube 50 terminated with two windows 52, 54 with crossed or parallel polarizers 8, 10 with the axis of polarization preferably at ~45° with respect to the optical axis of the birefringent material 4. Optional filters 14 or 16 could be also used. The tube 50 may be placed at an appropriate location inside a filter cartridge 40 for respiratory or filtration devices and the sensor may thus be used as an end-of-service-life indicator or dosimeter provided that a light source and a light detector are positioned at both ends of the perforated tube 50.

Referring to FIGS. 18A-B, an array of birefringent sensing elements 92 made of anisotropic materials 4 and mirrors 26 may be mounted in reflection mode on the side of the cartridge 40. The polarizer 8 may be a linear or a circular polarizer. The window 52 should be transparent to light from the desired light source and provide a mechanical barrier like the rest of the walls of the cartridge 40. The window 52 could be made for example from glass or from transparent plastic. The position of the polarizer 8 and the window 52 may be inverted. Note that the window 52 may advantageously have a pattern or filter that is designed to select preferably some angular orientations. This feature could advantageously be used to enhance reading contrast or to avoid unwanted light. An optional filter 16 could be used between the light source 6 and the light detector 12 if necessary. The different sensing elements are placed at different depths in the cartridge 40 in order to show the progression of the chemical vapors to be detected inside the packed adsorbent bed 42. Such an array of sensing elements 92 may be useful to give an estimation of the remaining life of adsorbent bed 42 that is still usable for safe respiratory protection and is thus a true remaining-life indicator.

The anisotropic material 4 may be a birefringent (totally or partially) porous glass which may be obtained by different methods such as by a sol-gel process, chemical vapor deposition (CVD) or acid leaching after thermal two-phase separation of glasses such as alkali borosilicate or Vycor™ glass, see U.S. Pat. Nos. 2,106,744, 2,221,709 and 2,286,275 (Hood et al.). In the case of phase separated glasses, the conditions of phase separation are preferably chosen to produce an open porous structure where chemicals such as organic vapors may easily condense. Such an open porous structure may conveniently be obtained by spinodal decomposition. The way a porous glass is produced strongly influences its final optical properties. For instance birefringence of porous-glass produced from two-phase alkali borosilicate is dependent on the chemical composition and on the geometrical shape of the initial glass, on the phase separation process (including factors such as temperature, time of the heat treatment and mechanical strain by stretching or by compression), on the leaching process (including factors such as temperature, time, nature and concentration of the chemicals used for leaching and stirring conditions) and on the post leaching treatments (including factors such as washing with water or dilute alkali solution and drying conditions). See e.g. Takamori, T., "Structural anisotropy and birefringence in microporous glasses", J. Am. Ceram. Soc. 61 No. 9-10, 1978, pp. 434-438. All of these parameters may be used to tune the final birefringence of the porous glass as required or desired. Suitable anisotropic materials may be constructed using commercially available porous glasses, but may not provide optimal performance with respect to for instance certain organic solvents (e.g. Vycor™ glass sold by. Corning Glass Inc. has been successfully tested with toluene, but the pores were found not to have optimal dimensions for maximum sensitivity).

Self-organized porous glass structures with optical anisotropy may also be obtained by other techniques such as sol-gel preparation. In some cases, after or during polymerization of silicate monomers, self-organization is achieved by the use of detergents in the presence of organic solvents which are removed by evaporation and calcination to produce the porous structured glass. A consolidation step before calcination may also be used to obtain a crack-free glass structure suitable for a commercial product. See e.g. Ryoo R. et al., "Optically transparent, single-crystal-like oriented mesoporous silica films and plates", J. Phys. Chem. B 101, 1997, pp. 10610-10613; and Ko C. H. et al., "Mesocrystal engineering using non-bonded interaction to obtain optically transparent mesoporous silica films and plates with uniform orientation", Micro. Meso. Mat. 21, 1998, pp. 235-243.

Under certain conditions glasses and other porous materials may become anisotropic and show birefringence as optical anisotropy. The most common cause of optical anisotropy is stress but many other causes have been reported such as "frozen-in strain" (Type I & II), "differential contraction of anisotropic phases", "chain orientation", "form birefringence", "distribution birefringence" and "anisotropic array of micropores". See e.g. Takamori, T. et al., "Anomalous birefringence in oxide glasses" in "Treatise on materials science and technology", Glass I Vol. 12, 1977, pp. 123-155, Tomozawa M. & Doremus R.H. Eds., Academic Press N.Y. Among the most interesting for the purpose of the present invention are the last three which are observed in borosilicate and Vycor™ brand glasses as well as in porous silicon.

Usually, for porous glasses, the observed birefringence is a combination of the effects of several types of inhomogeneities such as microcrystallization of secondary silica, strata formation or spindle-like inhomogeneities which are strongly dependent on the way the porous structure is obtained. See e.g. Antropova, T. V. et al., "Porous glass: inhomogeneities and light transmission", Opt. Appl. Vol. XXX No. 4, 2000, 553-567. The resulting birefringence is also often spatially distributed. See e.g.: Altshuler, G. B. et al., "Spatial dispersion of anisotropy of high-silica microporous glasses", Opt. Spektrosk. 63, 1987, 228-231; Altshuler, G. B. et al, "Porous glass optics", J. Non-Cryst. Solids 123, 1990, pp. 266-270; and Burkat, T. M. et al., "Structural anisotropy and birefringence in porous glass plates", Fiz. Khim. Stekla 17 No. 5, 1991, pp. 781-790. Such spatial distribution could be a problem for applications where integration on large surfaces is necessary, but in the present case, homogeneity in the order of the core size for multimode optical fibers (50-1000 μm) is relatively easy to achieve experimentally.

The porous birefringent glass preferably should be transparent or semi-transparent (e.g. opal glass) while being sufficiently transmissive to light to permit detection using for example the human eye, a photodiode or the like. One advantage of porous glasses over porous silicon is their better transparency to visible light which is valuable especially if the human eye serves as the light detector.

For an application where a light intensity change at a given wavelength $\lambda$ will be observed in the presence of a chemical substance to be detected, the thickness and birefringence preferably should be adjusted so that in the absence of the chemical substance, a maximum intensity or a maximum ratio of measured values is obtained from the sensor. Improved sensitivity may be achieved by selecting the initial intensity not at the maximum of the transmission spectrum, but in a region where the transmission spectrum changes rapidly with the wavelength $\lambda$, so that a small shift in the transmission spectrum due to the detection of the chemical substance will produce a large change in the transmitted intensity.

Figure 19:
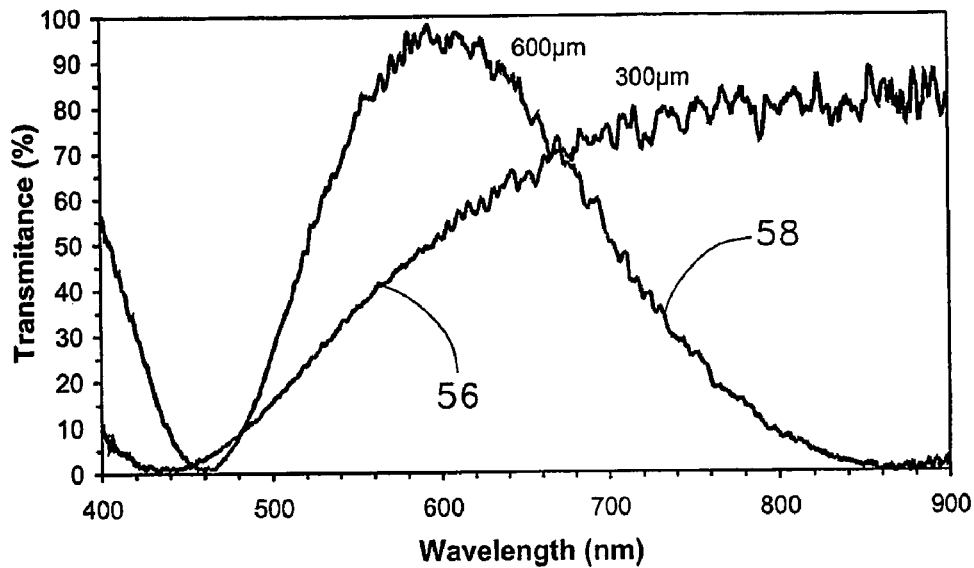
FIG. 19 is a graph illustrating transmitted power curves as a function of wavelengths for two different thicknesses of a birefringent porous glass.

Referring to FIG. 19, there is shown a graph of the experimental transmitted light spectrum obtained for a birefringent porous glass (thickness 300 μm as depicted by curve 56 or 600 μm as depicted by curve 58) placed at 45° between two crossed polarizing Glan-Thomson prisms (not shown). The porous glass structure was obtained from a leached phase-separated borosilicate glass using a process similar to the one described in U.S. Pat. No. 5,250,095 (Sigel, Jr. et al). Using the Braunauer, Emmett and Teller (BET) porosimetry, the surface area of the sample was found to be about 350 $m^2/g$ with a pore diameter distribution ranging from 2 nm to >60 nm and an average pore maximum diameter of about 3.5 nm. Scanning electron microscopy (SEM) micrographs of the freshly fractured surface of the leached glass also showed the presence of an interconnected porous structure. As shown in FIG. 19, the 300 μm thick polished porous glass sample (curve 56) has a transmission minimum around 440 nm and a maximum possibly around 850 nm whereas the 600 μm thick sample (curve 58) has two minima around 460 nm and 880 nm and a maximum around 600 nm. From such experimental results, a birefringence of $\Delta n \approx 1.5 \cdot 10^{-3}$ could be estimated for the porous glass sample. It is believed that for this glass the optical anisotropy may be related to the combinatory effect of the anisotropic shape of the pores with the orientation of secondary silica gel strata deposition occurring during the leaching step. This secondary silica gel could be partially removed by a short (5-20 min) gentle basic treatment such as diluted sodium hydroxide (NaOH 0.001-0.05 M) in order to avoid overly attacking the remaining silica rich matrix of the porous glass and thus changing the shape and size of the pores. Removing the secondary silica gel will generally increase the absolute value of the birefringence but may also increase the size of the pores as shown by BET porosimetry measurements, indicating that both possible origins of the anisotropy contribute to opposite sign birefringence. Interestingly in the presence of a chemical, capillary condensation could occur preferably where the curvature of the matrix wall is highest. In other words for a cylindrical pore with an oval cross-section, capillary condensation will first tend to fill the high curvature surfaces creating a more circular cross-section before filling the pore, possibly reducing the contribution of the pore shape to the anisotropy.

Figure 20:
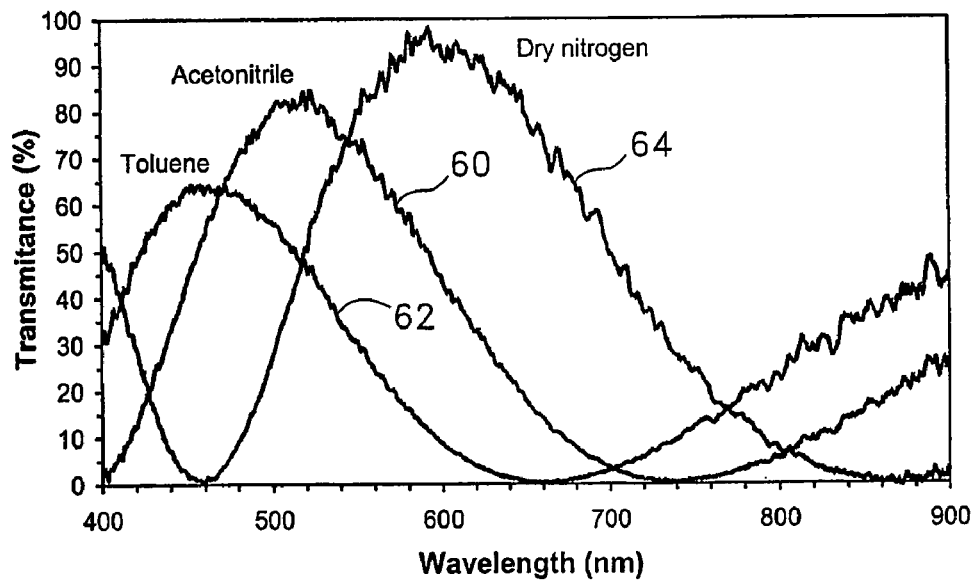
FIG. 20 is a graph illustrating transmitted power curves as a function of wavelength for a birefringent porous glass under different chemical conditions.

Referring to FIG. 20, in the presence of a chemical substance to be detected, the birefringence is reduced and the transmitted spectrum is thus shifted towards the smallest wavelengths. Using a 600 μm thick birefringent porous glass identical to the one in the experiment of FIG. 19, two organic solvent vapors are detected easily at 1000 ppm (in a nitrogen flow of 1 L/min). Acetonitrile (curve 60) induces a shift of the transmission maximum from ~600 nm for dry nitrogen (curve 64), down to ~515 nm ($\Delta\lambda$=85 nm). For toluene (curve 62) which condenses more easily inside the porous structure, the shift is even greater at ~460 nm (Δλ=140 nm). In both cases it has been observed that the shift is concentration dependant. The condensation of the organic vapors into the porous structure usually induces a reduction in birefringence and total transmitted light due to increased light diffusion by the sample as different pore size domains from the outside to the inside of the porous sample are filled and due to an increased total effective index of the porous glass as solvent vapors (n>1) take the place of air (n≈1) in the pores. It should be mentioned that the increase in light diffusion caused by the solvent could be a transitory phenomenon or not depending on the porous structure of the glass, and may be due to the creation of localized condensed vapors whose domains sizes are comparable to the size of the wavelengths and which may give rise to optical discontinuities. See e.g. Herman, P. H. in Colloid Science, 1949, Vol II, "Reversible systems", H.R. Kruyt Ed., Elsevier Pub., chap. XII §6 "Sorption and swelling", pp. 512-580]. Such phenomenon could be used in conjunction with phase shifting to increase the sensitivity of detection in cases where decreased light intensity is observed.

Figure 21:
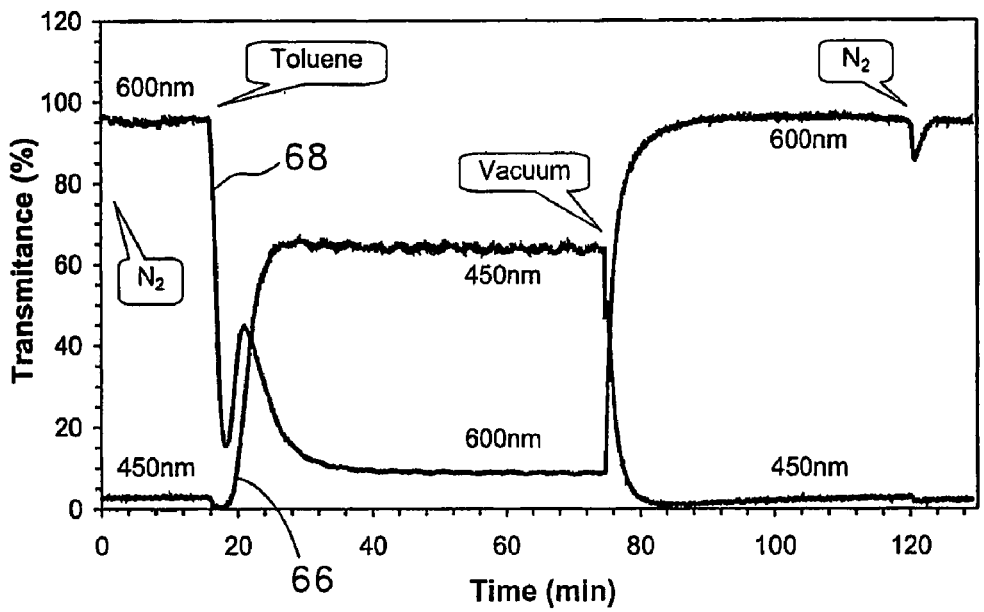
FIG. 21 is a graph illustrating transmitted power curves as a function of time for a birefringent porous glass under different chemical conditions.

Referring to FIG. 21 with an experimental design identical to the one of FIG. 19, there is shown transmittance variations with time at two different wavelengths (around an initial minimum at 450 nm as depicted by curve 66 and around an initial maximum at 600 nm as depicted by curve 68) of a 600 μm thick birefringent porous glass during intermittent contact with toluene vapors (1000 ppm in nitrogen flowing at 1 L/min). In the presence of toluene, the light intensity at 600 nm decreases rapidly down to ~15% of the initial intensity whereas at 450 nm, it increases rapidly from ~3% up to ~65% of the maximum intensity. The transition state kinetic may differ depending on the observation wavelength. For example at 600 nm the intensity initially drops rapidly due to the combined effects of birefringence diminution and transitory light diffusion. From about 2 to 5 minutes following toluene vapor initiation, the intensity increases as the diffusion transition state ends, then decreases down to a stationary state mainly due to a reduction in birefringence. At 450 nm, the intensity mainly increases up to a stationary level with almost no influence by transitory light diffusion since the initial transmission is close to zero. Condensation of toluene into the porous structure is reversible and the solvent may be removed by a flow of pure nitrogen or more rapidly by vacuum as shown in FIG. 21 where the initial intensity values are recovered quite rapidly. The kinetics depend mainly on the applied vacuum.

Figure 22:
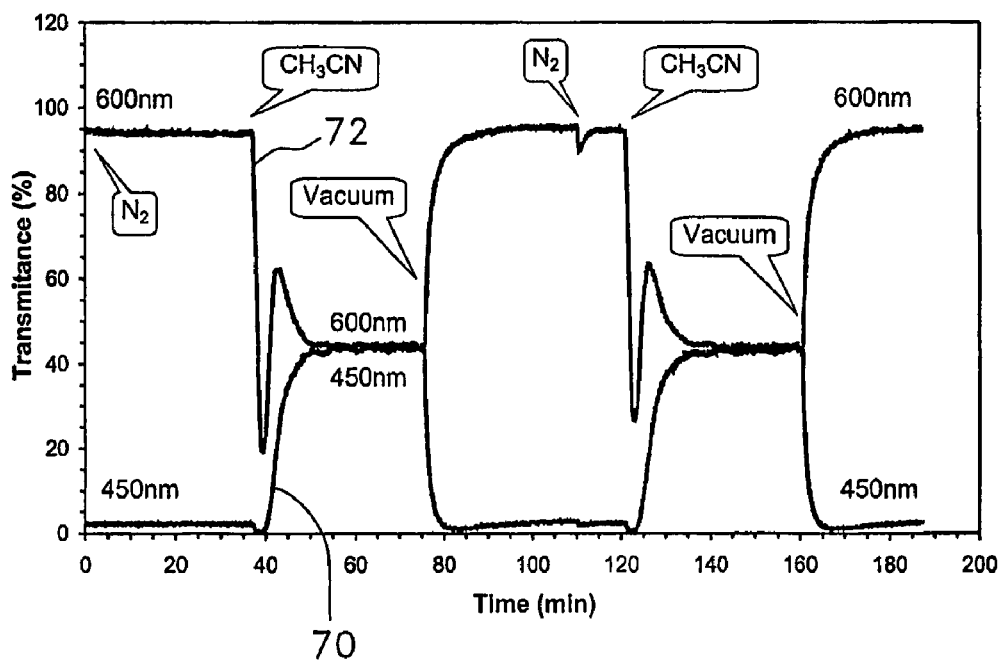
FIG. 22 is a graph illustrating transmitted power curves as a function of time for a birefringent porous glass under different transiting chemical conditions showing repeatability of the disclosed method.

Referring to FIG. 22 with an experimental design identical to the one of FIG. 19, there is shown the response with time of the FIG. 21 birefringent porous glass sample to 1000 ppm of acetonitrile (in nitrogen flowing at 1 L/min). The curves 70, 72 have a shape similar to the curves 66, 68 in FIG. 21 with a light intensity decrease at 600 nm (curve 72) and an increase at 450 nm (curve 70). The two curves reach a similar stationary light transmission at about 45% of the maximum intensity. The difference in stationary level compared to FIG. 21 may be explained by the reduction in birefringence which is less pronounced for acetonitrile than for toluene as seen in FIG. 20. As is the case for toluene, the condensation into the pores is reversible and the porous glass sensor may be intermittently exposed to solvent with very good reproducibility as shown in FIG. 22 where two cycles of contact with acetonitrile are presented.

For an application where a color change, e.g. green to red, is desired in the presence of a chemical substance to be detected, the thickness and birefringence of the anisotropic material (e.g. porous glass) may be tuned so that without the chemical substance to be detected, the transmitted spectrum of such a porous glass placed between two crossed polarizers will present a maximum of transmission in the green region (around 520-550 nm) and a minimum of transmission in the red region (around 610-750 nm). When illuminated by a green-red bicolor LED, the birefringent porous glass will look green in the absence of the chemical substance to be detected. In the presence of chemicals such as organic vapors that may condense into the porous structure, the birefringence of the glass will change (e.g. decreases), producing a change in the transmitted spectrum (e.g. shift toward shorter wavelengths). Less light will thus be transmitted in the green region and more light will be transmitted in the red region, producing a change in color from green to red as the pores fill with an increasing concentration of the chemical substance to be detected.

For color blind observers, optional green and red filters could be used to help indicate the effective color of the sensor and thus the presence of the chemical to detect.

Referring back to FIGS. 12A-C, for an application such as an end-of-service-life indicator for an organic vapor cartridge, a detecting element 4 made of birefringent porous glass mounted in transmission mode between the two multimode optical fibers 36, 38 with crossed polarizers 8, 10 may be used. The small optical fibers 36, 38 with the mounted sensing element 4 may easily be inserted directly inside an activated carbon bed 42 (or equivalent sorbent) without overly disturbing the flow inside the cartridge. A small encapsulating perforated or permeable tube may conveniently be provided to maintain the various elements in proper orientation. The fiber 36 is used for light input to the porous glass detecting anisotropic element 4 and the fiber 38 is used to collect the output light signal. The birefringent porous glass is preferably placed at 45° between the two fiber ends mounted with crossed polarizers 8, 10 such as Polaroid™ films. It should be noted that commercially available Polaroid™ films generally do not efficiently polarize wavelengths above approximately 800 nm. The output signal may be analyzed in many ways as mentioned above.

A simple version of an end-of-service-life indicator may include an inexpensive light source 6 such as a bi- or tri-color LED (or the like) driven by an electronic circuit (not shown) which switches the color alternatively at a constant intensity, inexpensive and robust optical fibers 36, 38 such as plastic optical fibers or the like (e.g. light pipes or simple transparent plastic tubes) which direct the light by transillumination through the porous glass fiber or slab 4 (placed at 45° between the two crossed polarizers 8, 10) to a photodetector 12 such as a photodiode. An electronic circuit (not shown) connected to the photodetector 12 may be provided to follow the output intensity in synchronicity with the colored light source 6 and to trigger an alarm (e.g. a visual or audio alarm) to warn the end user as soon as a significant intensity variation is detected or when the colored intensity ratio reaches a predetermined level. An advantage of having at least a dual color light source is that possible light fluctuations due to the source or other mechanical elements may be taken into account, thus reducing the possibility of false alarms. The intensities could also be logged into a memory unit for data analysis.

Electronic detection may be unnecessary and a simple visual detection may be achieved if the porous glass detecting element is properly chosen so that it transmits preferably one color and attenuates another color of the light source in the absence of chemicals and does the opposite in the presence of the chemical substance to be detected.

If the above-mentioned green to red color change in the presence of solvent is desired for a straightforward interpretation of the sensor status, it may be advantageous that one of the maxima of transmission of the porous fiber without solvent be at (or near) the green region (say at around 520 nm) and that one of its minima be at or near the red region (say at 630 nm). According to equation (3) above, this situation is possible at $\lambda/=520$ nm when the order values of the birefringence are m=2 or preferably m=3. If a d=1 mm thick transilluminated birefringent porous fiber is considered (note that this physical parameter could easily be changed if necessary), the birefringence should be around $|\Delta n| \approx 1.3 \cdot 10^3$ for m=2 and around $|n| \approx 1.82 \cdot 10^{-3}$ for m=3, which may easily be achieved experimentally e.g. for birefringent porous glass. Using value of m=1 will give $|\Delta n| \approx 0.78 \cdot 10^3$ and m=4 will give $|\Delta n| = 2.33 \cdot 10^{-3}$, which will produce smaller red-green contrasts and may be less desirable. For values of m=2 or m=3, the minimum transmission given by equation (4) above in the red region of the spectrum is at $\lambda=650$ nm for m=2 and at $\lambda=607$ nm for m=3, which are values close to $\lambda=630$ nm. The color of such a sensor in the absence of chemicals to be detected will be more green than red. When the porous fiber is in the presence of e.g. an organic solvent, the absolute value of the birefringence may decrease. A maximum color contrast may be obtained when the transmission spectrum at $\lambda=520$ nm through the porous fiber becomes a minimum of transmission in the presence of solvent, e.g., when $|\Delta| \approx 1.04-10$ for m=2 and $|\Delta n| \approx 1.56 \cdot 10^{-3}$ for m=3 (corresponding to a birefringence variation of 20% and 13.9% respectively). It can be noted that the higher the m value, the lower the birefringence variation needed for a given spectral shift, and that highly birefringent materials could have higher sensitivity. In the presence of solvent, maxima of transmission in the red region are obtained at $\lambda=693$ nm and $\lambda=624$ nm respectively, which are close to $\lambda=630$ nm and the color of the sensor will thus be more red than green.

In order to increase contrast in this example when a white light source such as daylight is used, an optional yellow high pass filter 14 filtering out the wavelengths below 500 nm may advantageously be used to remove the contribution in the blue region of the birefringent material which otherwise would lead in the presence of solvent to a purple color instead of the desired red color. With such a filter and in the presence of solvent, a maxima of transmission that will be at $\lambda=416$ nm or at $\lambda=446$ nm respectively will be filtered out, whereas in the absence of solvent, a minima of transmission will be in the blue region at $\lambda=433$ nm and $\lambda=455$ nm respectively and the presence of the filter 14 will not be detrimental. In order to increase contrast and to avoid transmitted light in the blue region of the visible spectrum and the need for a high pass yellow filter 14, a red (630 nm) green (520 nm) bicolor LED may advantageously be used as the light source 6. In that case, the light intensity of the two LED colors could also be adjusted in order to compensate for human eye color perception and thus increase contrast perception. Because the eye is less sensitive in the red than in the green, the red light intensity preferably is greater than the green S intensity. In order to improve resolution, a narrow band LED preferably should be used. Commercial LEDs with typical 30-40 nm half height widths should be suitable. Narrower light sources 6 such as single wavelength sources (e.g. lasers) may be better but their cost will usually be higher. Such sources may however be useful in cases where the product $d \cdot |\Delta n|$ is high (say above $5 \cdot 10^{-3}$ mm) in order to avoid overlapping birefringence orders within the spectral width of the light source 6. For laser sources, one may also take advantage of the fact that light emission can already be linearly polarized, possibly avoiding the need for the first polarizer 8 if this polarization is preserved at the anisotropic material 4.

Figure 23:
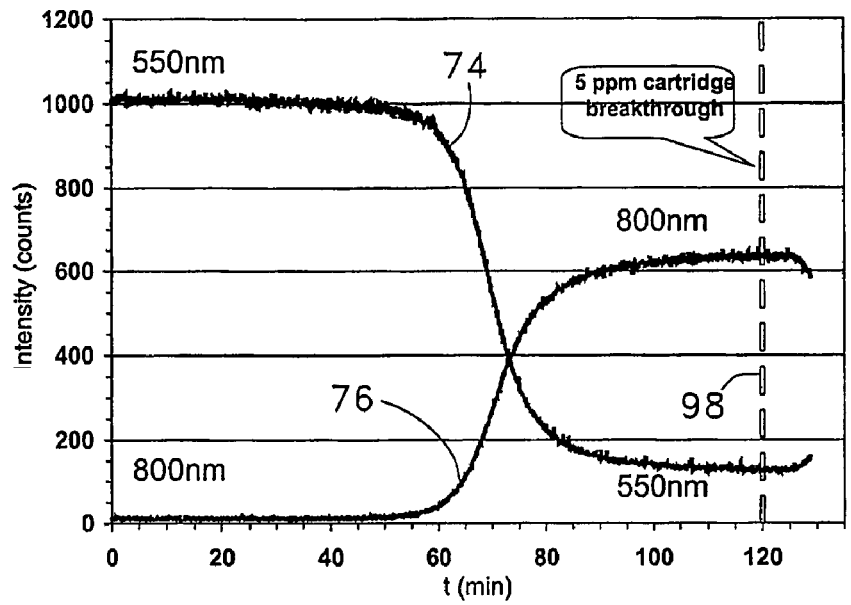
FIGS. 23-25 are graphs respectively illustrating variation intensity curves measured at 550 nm and 800 nm of an optical birefringent porous glass sensing element inserted in an activated carbon bed of an organic vapor cartridge, and corresponding intensity ratio curves and spectra.
Figure 24:
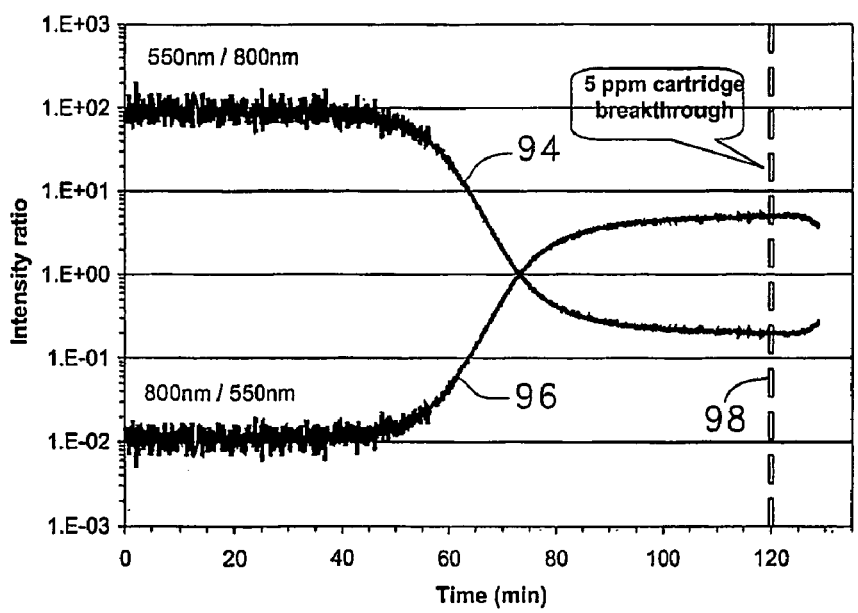
Figure 25:
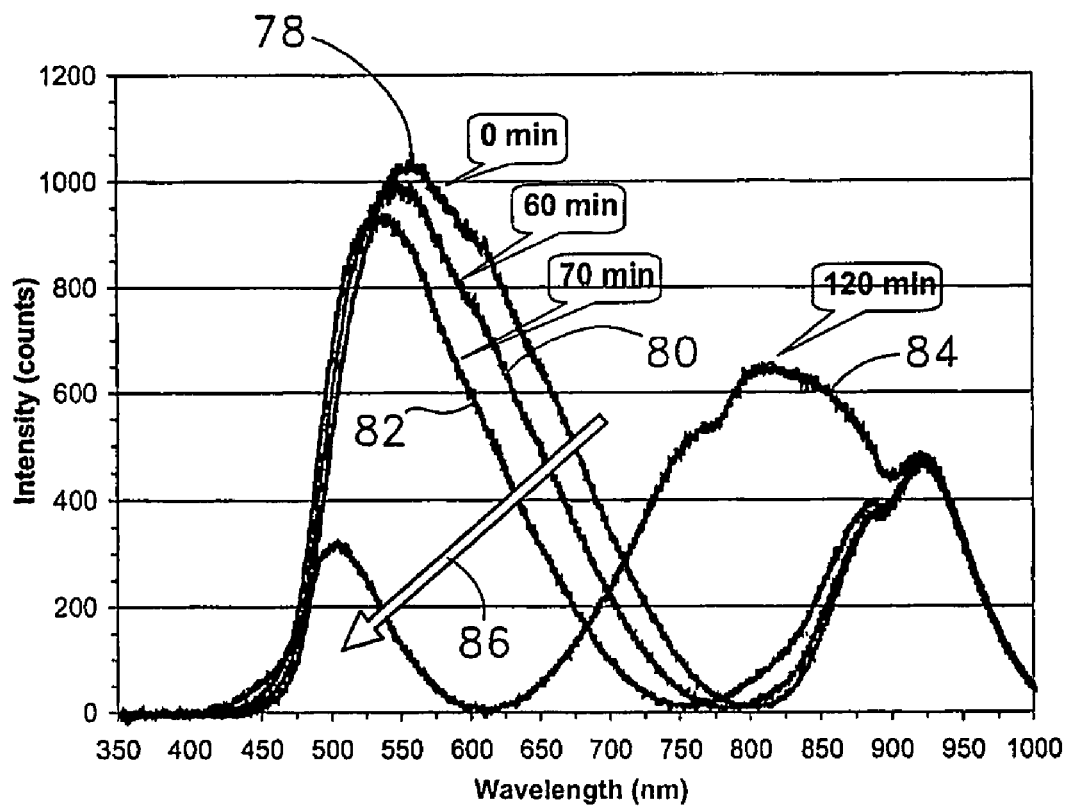

Referring to FIGS. 23, 24 and 25, there are shown the results obtained with a sensor inside a commercial organic vapor cartridge filled with 46 g of water vapor activated porous carbon 42. The anisotropic material 4 of the sensor was a porous glass round fiber similar to that used in FIG. 21 and 22 except that the diameter was about 1 mm. Using optical fibers, the sensor is transilluminated with a white light tungsten halogen lamp (2800° K) and the output light is analyzed using an optical fiber spectrometer (1 nm resolution) that records over time the light intensity at different wavelengths. The cartridge is challenged at t=0 min with 1000 ppm of toluene in air flowing at 32 L/min which corresponds generally to the average respiration of a human performing a heavy work. To determine the effective breakthrough of the cartridge, the air coming out of the cartridge is continuously analyzed by a gas chromatograph in order to track the increase in toluene. The breakthrough time is determined when more than 5 ppm of toluene is detected in the outgoing air and corresponds to approximately 120 min. for the experimental conditions. The 5 ppm breakthrough time is indicated by a dashed line 98 in the two FIGS. 23 and 24.

Referring to FIG. 23, there is shown the intensity change measured at two different wavelengths (550 nm as depicted by curve 74, corresponding to a maximum of transmission for the birefringent porous glass in the absence of toluene, and 800 nm as depicted by curve 76, corresponding to a minimum of transmission). The intensities at the two wavelengths do not vary until the toluene reaches, at about. 60 min., the birefringent porous glass detecting element positioned approximately at half the depth of the activated carbon. After 120 min. of challenge, the intensity at 550 nm decreases steadily to a plateau at approximately 10% of the initial value whereas the intensity at 800 nm increases regularly to a factor of about 50 of its initial value.

Referring to FIG. 24, there is shown the intensity ratios (logarithmic scale) with time (curves 94 and 96 are intensity ratios of 550 nm/800 nm and 800 nm/550 nm respectively). When combined together for a better sensitivity, at 120 min. a ratio of about 500 is achieved for the FIG. 23 sensor, which can facilitate detection of breakthrough indicating the end-of-service-life of the cartridge.

Referring to FIG. 25, there is shown the spectra measured between 350 and 1000 nm at different times of the challenge test: 0 min. initial spectrum before toluene detection as depicted by curve 78; 60 min. and 70 min. during the transition state of toluene front detection inside the cartridge as depicted by curves 80 and 82; and at 120 min. corresponding to 5 ppm breakthrough of the cartridge as depicted by curve 84. It can be seen that the spectra are shifted towards lower wavelengths (depicted by arrow 86) and that the minimum of transmission shifted from 800 nm to about 600 nm when the birefringent porous glass detecting element was saturated with probably more than 1000 ppm of toluene.

To avoid false solvent detection in particularly humid environments, the porous glass could be surface treated to make it hydrophobic. Numerous hydrophobic treatments are described in the literature and include coating, dipping and liquid or vapor phase reaction with hydrophobic agents. Hydrophobic agents are easily available commercially from several companies that specialize in surface modifying reagents.

Hydrophobic treatments of porous materials will change the surface tension as well as the porous structure of such materials, especially in the microporous range (pore diameter below 2 nm). The way the hydrophobic treatment is processed may have an important impact on the final structure. See e.g.

Foltynowicz, Z. et al., "Effect of silane treatment on the pore structure of porous glasses", Glass Technology Vol. 34 No. 5, 1993, pp. 206-209.

A good knowledge of how the porosity is affected by the hydrophobic treatment is valuable and may help in designing an optimal porosity distribution profile and in producing a more sensitive porous anisotropic material. It should also be mentioned that hydrophobic treatments may affect anisotropy and may be used to tune the final properties of the sensor. Surface chemistry modifications (e.g. silica surface modifications developed for chromatography purposes) may also be used to change surface energy and to promote selective detection of a chemical or a class of chemicals by the anisotropic material.

Indeed, in the application of the sensor such as an end-of-service-life indicator for an organic vapor cartridge, the birefringent porous glass preferably has the ability to condense a wide variety of organic solvents. This ability may be directly related to the pore diameter, the topology (e.g. porosity distribution or pore shape) or the surface energy (e.g. surface tension) of the porous glass which may be tuned as already mentioned at several steps of the fabrication process using techniques such as spinodal decomposition, chemical treatments, hydrophobic surface treatments, partial sintering by heat treatments once the glass is porous and the like. Various techniques for controlling the pore size are described in the literature including those developed for controlled pore glass (CPG) production. Although narrow pore size distribution may be an advantage for some sensing applications where size exclusion may be used for discrimination of the detected molecules, in the case of an end-of-service-life indicator, a broad pore size distribution is more desirable to enable the capillary condensation of e.g. organic solvents with varied molecular volumes. It is believed that to promote capillary condensation of most common organic solvents, the pore diameters preferably are in the range of 1-100 nm (micro- and mesopores) and more preferably around 1-10 nm. The smallest micropores (namely pore diameter below 2 nm) should preferably be avoided, in order to reduce the capillary condensation of water. Water is one of the smallest solvent molecules and its condensation is not desirable in an end-of-service-life detecting application which should be insensitive to humidity. Surface treatments may be used when small pore diameters can not be otherwise avoided.

Since the sensitivity of the sensor is directly related to a solvent's ability to condense into the pore structure of e.g. the birefringent porous glass, high boiling point solvents are usually the easiest to detect. Sensitivity may thus be better for high boiling point solvents than for low boiling point solvents. However, many common organic solvents including low boiling point solvents such as diethylether (Bp=34.6° C.), dichloromethane (Bp=40° C.) or acetone (Bp=56° C.) may be detected by the sensor using birefringent porous glass.

For special applications, multiple sensing elements may be implemented at different levels in the carbon bed as shown in FIGS. 18A-B. Multiple sensing elements may thus inform the user about the progression of the solvent front inside the cartridge (and the remaining time for a safe use) or may inform the user about solvents having different detection levels. For example specially designed porous glass sensing elements for difficult-to-detect solvents may be placed closer to the inlet of the cartridge and other glass sensing elements for easy-to-detect solvents may be placed closer to the outlet of the cartridge.

It has been mentioned that the response time of the sensor is dependent on the diffusion time of solvent vapors inside the porous structure. Small diameter birefringent porous glass fibers may thus be advantageous for fast response. However since filtration cartridges are usually used for at least several hours, slower response times (e.g. ranging from 5 min. to 20 min.) often will be acceptable and may easily be experimentally achieved as shown in FIGS. 21 and 22. If faster response time is desired, configurations using reflected light may be used. It should also be noted that a detectable change in the transmitted or reflected light is usually measured well before the solvent equilibrium inside the porous glass fiber is achieved. Thus, although such a sensor could theoretically be used at equilibrium for concentration determination if a calibration curve has been established, an end-of-service-life indicator should detect signal variations and measurements at equilibrium are not mandatory for such an application.

Porous glass may experience some ageing phenomena: for example clear porous glass may turn yellow when exposed to ambient air for months. It is believed that this phenomenon is related to chemisorption of volatile compounds normally present in air such as carbon dioxide. Such normal ageing might arise in an ambient air sensor but may be less likely in an end-of-service-life indicator since the birefringent porous glass is protected from contamination by the respirator cartridge itself.

Usually, optical polymers are amorphous isotropic materials but anisotropic optical polymers may be obtained in different ways, either by orienting monomers (e.g. by crystallization, magnetical or mechanical forces) and polymerizing them in their oriented state, or by orienting isotropic polymers and creating anisotropy by the influence of physical forces (e.g. by mechanical forces such as stretching, electrical field or even optical effects). Such anisotropy usually arises due to orientation of strong polarizable substituents and may either be static or dynamic. Depending on the nature of the substituents, positive birefringent polymers such as polyvinylchloride (PVC) or polycarbonate (PC) or negative birefringent polymers such as polymethyl methacrylate (PMMA) or polystyrene (PS) may be obtained by mechanical alignment of polymeric chains during stretching. Copolymers of positive and negative birefringent components (such as but not limited to allyl and methacrylic monomers) may be synthesized in order to modulate the birefringence behaviour. See e.g. Lorkowski H-J et al., "Optical polymers with special birefringent properties", Polymers for Advanced Technologies Vol. 7, 1996, pp. 501-506. Many types of polymers may present optical anisotropy and are described in the literature. Many polymers may easily swell or shrink in the presence of chemicals such as organic solvents, especially non-reticulated polymers which have greater chain mobility. Thus birefringent non-opaque polymers may be used as sensing materials in the present invention. Variation of the thickness of the birefringent polymer due to swelling or shrinkage will cause a phase shift of one polarization state relative to another polarization state in propagating light and may be detected by a light detector 12 if the thickness variation is sufficient. Anisotropic polymers with high swelling properties are preferably selected. Since swelling properties are usually strongly dependent on the physical and chemical nature of the interacting molecules (e.g., the anisotropic polymer matrix and the diffusing molecules to be detected), sensors to specific molecules (or molecule classes) may be designed by correctly selecting the anisotropic polymer. For multiple detections, an array of different polymers may be used.

It should be mentioned that swelling of polymers may also affect birefringence and in order to avoid a compensation effect, it would be thus advantageous that the two factors (thickness and birefringence) do not move in countervailing directions since the phase shift is the product of the two factors.

It should also be noted that during the swelling of polymers, some relaxation effects may take place or be accelerated due to higher molecular motion. Such relaxatiorin may decrease the anisotropy irreversibly and may be a disadvantage for reversible sensors, but also may be an advantage for some applications where irreversibility is desirable.

The anisotropic material may also be a birefringent polymer such as low density polyethylene (LDPE) that has been stretched in order to orient the polymeric chains and to create optical anisotropy. By this method, high birefringence may be obtained (e.g. an absolute birefringence of $|\Delta n| \approx 3 \cdot 10^{-2}$). For instance, a 70 μm birefringent polyethylene film whose stretched axis is placed preferably at 45° between two crossed polarizers may be used to detect, by variations in the transmitted light spectrum, the presence of organic solvents such as toluene which diffuse easily inside the polymer.

Since molecule diffusion in polymers is usually a slow process, thin polymer films (e.g. up to about 100 μm) may be preferable in order to reach the equilibrium state more quickly. Highly birefringent polymers may compensate for low thickness films in order to produce sufficient phase shift in the presence of a chemical substance to be detected to enable intensity variation measurement at different wavelengths. Advantageously porous polymers made by different techniques known by people in the art may be also used to increase surface interaction as well as kinetics of diffusion. See for instance Li Y. Y. et al. "Polymer replicas of photonic porous silicon for sensing and drug delivery applications" Science Vol. 299, 2003, pp. 2045-2047. Such porous anisotropic polymers may present interesting mechanical and chemical stability properties useful for designing stable and robust chemical sensors.

The above disclosed method and sensor may be highly sensitive, and the sensor may be simple in construction, inexpensive and robust. The method and sensor may be used to detect numerous chemical species. The method and sensor are particularly well adapted for making end-of-service-life or remaining-life indicators for air-purifying devices, and dosimeters for air monitoring, using sensors ("embedded sensors") that are at least partly surrounded by absorbent particles. If care is taken in selecting an embedded sensor (preferably a porous embedded sensor) and a mass of absorbent particles having an appropriate pore diameter, the resulting combination appears to provide substantially greater sensitivity than may be obtained using a bare sensor.

The disclosed method thus comprises the steps of subjecting the anisotropic material 4 to the analyte 2 possibly containing the chemical substance, passing light through the anisotropic material 4, collecting at least a portion of the passed light, and detecting a change in an optical anisotropy of the collected light, the change being indicative of the chemical substance in the analyte 2. The optically anisotropic material 4 may be at least partially surrounded by absorbent particles 42 (as shown e.g. in FIGS. 16A through 18B). Visible light may be passed through the optically anisotropic material 4, and a polarization state is detected. The optically anisotropic material 4 may be other than porous silicon.

While embodiments of this invention have been illustrated in the accompanying drawings and described above, it will be evident to those skilled in the art that changes and modifications may be made therein without departing from the essence of this invention. All such modifications or variations are within the scope of the invention as defined by the claims appended hereto.

The invention claimed is:

1. A method for indicating an end of life of a respirator cartridge, an air purifying cartridge or a filtration cartridge by detecting a chemical substance in an analyte, comprising steps of:
providing an optically anisotropic material forming a porous fiber or slab in a sorbent bed of the respirator cartridge, air purifying cartridge or filtration cartridge;
subjecting the sorbent bed to the analyte;
passing visible light through the anisotropic material by transilluminating the anisotropic material with the light;
collecting at least a portion of the passed visible light; and
detecting a change in a polarization state of the collected visible light, the change being indicative of the chemical substance in the analyte having reached the anisotropic material through the sorbent bed.

2. The method according to claim 1, comprising positioning the anisotropic material in a flowing course of the analyte.

3. The method according to claim 1, comprising directing light produced by a light source through the anisotropic material.

4. The method according to claim 3, comprising optically coupling the light source to the anisotropic material using a waveguide positioned between the light source and the anisotropic material.

5. The method according to claim 1, comprising optically coupling the anisotropic material to an optical detector.

6. The method according to claim 1, comprising transmitting the collected light through a waveguide between the anisotropic material and the optical detector.

7. The method according to claim 1, comprising tuning pore diameter, porosity distribution or pore shape of the porous optical material to alter detection sensitivity or selectivity.

8. The method according to claim 1, wherein the porous optical material comprises porous glass, porous silicon or porous polymer.

9. The method according to claim 1, wherein the change in the polarization state is porosity induced.

10. The method according to claim 1, wherein the optical path through the anisotropic material is at least $10^{-7}$ meters.

11. The method according to claim 1, wherein the optical path through the anisotropic material is less than $10^{-2}$ meters.

12. The method according to claim 1, comprising analyzing the collected light to determine an optical birefringence of the anisotropic material.

13. The method according to claim 12, comprising detecting a color or phase shift in the collected light.

14. The method according to claim 1, wherein the anisotropic material is between two polarizers.

15. The method according to claim 12, comprising comparing intensities of the collected light at different wavelengths.

16. The method according to claim 12, wherein the anisotropic material comprises an optically birefringent multilayer porous thin film.

17. The method according to claim 12, wherein the anisotropic material comprises an optically birefringent polymer, an optically birefringent polymer composite, or an optically birefringent multilayer polymer film, the optical birefringence of the anisotropic material changing in the presence of the chemical substance due to swelling of the anisotropic material.

18. The method according to claim 1, comprising analyzing the collected light to determine a dichroism of the anisotropic material.

19. The method according to claim 18, wherein the anisotropic material comprises an optically dichroic polymer, an optically dichroic polymer composite, or an optically dichroic multilayer polymer film, the dichroism of the anisotropic material changing in the presence of the chemical substance due to swelling of the anisotropic material.

20. The method according to claim 19, comprising measuring intensity changes of the polarization state of the collected light.

21. The method according to claim 19, comprising measuring changes in a ratio of the intensities of two mutually orthogonal polarization states of the collected light.

22. The method according to claim 1, comprising analyzing the collected light to determine a selective absorption thereof by the anisotropic material.

23. The method according to claim 1, comprising analyzing the collected light to determine an optical anisotropic diffusion thereof by the anisotropic material.

24. The method according to claim 23, wherein the collected light exhibits polarization-dependent scattering, and comprising measuring changes in the intensity of the polarization state of the collected light.

25. The method according to claim 23, wherein the collected light exhibits polarization-dependent scattering, and comprising measuring changes in a ratio of the intensities of two orthogonal polarization states of the collected light.

26. The method according to claim 23, comprising measuring a geometric distribution of the collected light in two mutually orthogonal directions.

27. The method according to claim 1, comprising analyzing the collected light for determining an anisotropic scattering thereof by the anisotropic material.

28. The method according to claim 27, wherein the collected light exhibits polarization-dependent scattering, and comprising measuring changes in the intensity of a polarization state of the collected light.

29. The method according to claim 27, wherein the collected light exhibits polarization-dependent scattering, and comprising measuring changes in a ratio of the intensities of two orthogonal polarization state of the collected light.

30. The method according to claim 27, comprising measuring a geometric distribution of the light collected in two mutually orthogonal directions.

31. The method according to claim 1, wherein there is a hydrophobic agent or treatment on the anisotropic material.

32. The method according to claim 1, wherein there is a surface treatment on the anisotropic material to promote selective detection of the chemical substance or a class of chemical substances thereof by the anisotropic material.

33. The method according to claim 1, further comprising selecting a wavelength range of the light prior to passing the light through the anisotropic material.

34. The method according to claim 33, wherein there is a filter in an optical path followed by the passed light.

35. The method according to claim 1, comprising filtering the collected light to enhance signal contrast or cut unwanted wavelengths.

36. The method according to claim 35, wherein there is a filter in an optical path followed by the collected light.

37. The method according to claim 1, comprising polarizing the light prior to passing the light through the anisotropic material.

38. The method according to claim 37, comprising linearly polarizing the light.

39. The method according to claim 38, wherein the anisotropic material comprises a birefringent material, an optical axis of which is placed in a propagation plane of the light at an angle with respect to a direction of the linear polarization.

40. The method according to claim 39, wherein the angle is substantially 45°.

41. The method according to claim 39, wherein there is a linear analyzer in an optical path followed by the collected light.

42. The method according to claim 41, comprising crossing the linear analyzer with respect to the linear polarization, thereby transmitting light that has been rotated by the birefringent material.

43. The method according to claim 41, comprising generally aligning the linear analyzer optical axis in parallel with respect to the linear polarization.

44. The method according to claim 37, comprising reflecting the passed light back through the anisotropic material prior to collecting the passed light.

45. The method according to claim 44, comprising reflecting the passed light on a reflective interface adjacent a side of the anisotropic material.

46. The method according to claim 45, wherein the reflective interface comprises a reflective material contacting the anisotropic material.

47. The method according to claim 45, wherein the light passes through a linear polarizer and is subjected to linear polarization before passing through the anisotropic material, and wherein the collected light passes through a linear analyzer.

48. The method according to claim 47, wherein the linear polarizer and the linear analyzer are integral with the anisotropic material.

49. The method according to claim 44, comprising producing multiple reflections of the passed light through the anisotropic material.

50. The method according to claim 49, wherein facing reflective interfaces on generally opposing sides of the anisotropic material produce the multiple reflections.

51. The method according to claim 47, wherein the light passes through a retardation plate between the linear polarizer and the anisotropic material and between the anisotropic material and the linear analyzer.

52. The method according to claim 37, comprising:
partially reflecting the passed light to produce reflected and transmitted passed light beams, collecting the reflected and transmitted light beams, using a parallel or perpendicular analyzer in an optical path followed by the reflected light beam, and a perpendicular or parallel analyzer in an optical path followed by the transmitted light beam; and
measuring intensities of the reflected and transmitted light beams, respectively, and analyzing a ratio thereof.

53. The method according to claim 52, comprising passing the reflected light beam through the anisotropic material prior to collecting the reflected light beam.

54. A sensor for indicating an end of life of a respirator cartridge, an air purifying cartridge or a filtration cartridge by detecting a chemical substance in an analyte, comprising:
an optically anisotropic material forming a porous fiber or slab provided in a sorbent bed of the respirator cartridge, air purifying cartridge or filtration cartridge, the sorbent bed to be subjected to the analyte;
a light supply passing visible light through the anisotropic material by transilluminating the anisotropic material with the light;
a collector capturing at least a portion of the passed visible light; and a detector characterizing or quantifying a change in a polarization state of the collected visible light, the change being indicative of the chemical substance in the analyte having reached the anisotropic material through the sorbent bed.

55. The sensor according to claim 54, wherein the light supply comprises a waveguide optically coupled to the anisotropic material.

56. The sensor according to claim 54, wherein the collector comprises a waveguide optically coupled to the anisotropic material.

57. The sensor according to claim 54, wherein the light supply and the collector comprise a common optical arrangement including a reflective interface adjacent a first side of the anisotropic material, and an optical fiber optically coupled to the anisotropic material on a second side thereof opposite the first side.

58. The sensor according to claim 54, wherein:
the light supply comprises a polarizer; and
the collector comprises an analyzer.

59. The sensor according to claim 54, comprising a perforated or permeable tube having first and second end windows, the anisotropic material being positioned in the tube, the first end window being provided with a polarizer, the second end window being provided with an analyzer.

60. The sensor according to claim 59, wherein the perforated or permeable tube is inside a filter cartridge for respiratory or filtration devices.

61. The sensor according to claim 54, wherein the light supply comprises a window and a polarizer adjacent the window, the anisotropic material being viewable through the window, the sensor having at least one reflective interface that reflects light through the anisotropic material towards the window.

62. (Currently Amended The sensor according to claim 61, wherein the anisotropic material is divided into sensing elements positioned at different depths in the sorbent bed to show progression of the chemical substance through the bed.

63. The sensor according to claim 54, comprising a permeable tube or membrane containing the anisotropic material.

64. The sensor according to claim 54, wherein the anisotropic material has a treated surface promoting selective detection of the chemical substance or a class of chemical substances.

65. The sensor according to claim 54, wherein the anisotropic material is embedded in the sorbent bed.

66. The sensor according to claim 54, wherein the optically anisotropic material is at least partially surrounded by absorbent particles contained in a housing having an inlet and an outlet defining a flowing course of the analyte, the anisotropic material being positioned in the flowing course of the analyte.

67. The sensor according to claim 54, wherein the light supply comprises a light source producing light passing through the anisotropic material.

68. The sensor according to claim 67, wherein the light supply comprises a waveguide optically coupling the light source to the anisotropic material.

69. The sensor according to claim 54, wherein alteration in pore diameters, porosity distribution or pore shape of the anisotropic material will alter the detection sensitivity or selectivity of the sensor.

70. The sensor according to claim 54, wherein the anisotropic material comprises porous glass, porous silicon or porous polymer.

71. The sensor according to claim 54, wherein the optical path through the anisotropic material is at least $10^{-7}$ meters.

72. The sensor according to claim 54, wherein the optical path through the anisotropic material is less than $10^{-2}$ meters.

73. The sensor according to claim 54, wherein the anisotropic material comprises an optically birefringent multilayer porous thin film.

74. The sensor according to claim 54, wherein the anisotropic material comprises an optically birefringent polymer, an optically birefringent polymer composite, or an optically birefringent multilayer polymer film, an optical birefringence of the anisotropic material changing in the presence of the chemical substance due to swelling of the anisotropic material.

75. The sensor according to claim 54, wherein the anisotropic material comprises an optically dichroic polymer, an optically dichroic polymer composite, or an optically dichroic multilayer polymer film, a dichroism of the anisotropic material changing in the presence of the chemical substance due to swelling of the anisotropic material.

76. The sensor according to claim 54, wherein there is a hydrophobic agent or treatment on the anisotropic material.

77. The sensor according to claim 54, wherein there is a surface treatment on the anisotropic material to promote selective detection of the chemical substance or a class of chemical substances by the anisotropic material.

78. The sensor according to claim 54, wherein the light supply comprises a filter in an optical path followed by the light.

79. The sensor according to claim 54, wherein the collector comprises a filter in an optical path followed by the collected light.

80. The sensor according to claim 54, comprising a reflective interface adjacent the anisotropic material reflecting the passed light back through the anisotropic material to the collector.

81. The sensor according to claim 54, comprising reflective interfaces adjacent generally opposing sides of the anisotropic material which produce multiple reflections of the passed light.

82. The sensor according to claim 58, further comprising a retardation plate between the polarizer and anisotropic material and between the anisotropic material and analyzer.

83. The sensor according to claim 54, comprising:
a partially reflective interface adjacent the anisotropic material to produce reflected and transmitted passed light beams, the collector capturing the reflected and transmitted light beams using a parallel or perpendicular analyzer in an optical path followed by the reflected light beam and a perpendicular or parallel analyzer in an optical path followed by the transmitted light beam.

84. The sensor according to claim 83, wherein the reflected light beam passes through the anisotropic material prior to capture.

85. The sensor according to claim 54, wherein the detector comprises the human eye.

86. The sensor according to claim 54, wherein the detector comprises a photoelectronic device.

87. The sensor according to claim 54, wherein the detector comprises a spectrophotometer.

88. The sensor according to claim 54, wherein the detector comprises a photodiode.

89. The sensor according to claim 67, wherein the light source comprises ambient light.

90. The sensor according to claim 67, wherein the light source comprises a light emitting diode.

91. The sensor according to claim 90, wherein the light emitting diode provides at least two colors.

* * * * *